US006849610B1

United States Patent
Liu et al.

(10) Patent No.: US 6,849,610 B1
(45) Date of Patent: Feb. 1, 2005

(54) POLYNUCLEOTIDE LIGANDS AS ANTIVIRAL AGENTS

(75) Inventors: Fenyong Liu, Berkeley, CA (US); Jun Wang, Houston, TX (US); Hong Jiang, Augusta, GA (US)

(73) Assignee: The Regents of the University of California, Oakland, CA (US)

( * ) Notice: Subject to any disclaimer, the term of this patent is extended or adjusted under 35 U.S.C. 154(b) by 112 days.

(21) Appl. No.: 09/721,543

(22) Filed: Nov. 21, 2000

Related U.S. Application Data

(60) Provisional application No. 60/167,509, filed on Nov. 24, 1999.

(51) Int. Cl.[7] ........................ A61K 31/70; A01N 43/04; C07H 21/04
(52) U.S. Cl. ........................................ 514/44; 536/23.1
(58) Field of Search ........................ 514/44; 435/91.21; 536/23.1

(56) References Cited

U.S. PATENT DOCUMENTS 5,523,389 A  *  6/1996  Ecker et al. ................ 536/23.1
5,856,085 A  *  1/1999  Wang et al. ..................... 435/5

OTHER PUBLICATIONS

Pan et al., Isolation of virus–neutralizing RNAs from a large pool of random sequences, 1995, Proc. Natl. Acad. Sci. USA, vol. 92, pp. 11509–11513.*
Wyllie, Susan (1999), "Single Channel Analysis of Recombinant Major Outer membrane Protein Porins from Chlamydia Psittaci and Chlamydia Pneumoniae." *FEBS Letters*, vol. 445:192–196.
Allen, Judith (Jul. 15, 1991), "A Single Peptide from the Major Outer Membrane Protein of Chlamydia Trachomatis Elictis T Cell Help for the Production of Antibodies to Protective Determinants." *Journal of Immunology*, vol. 147:674–679.
Wyllie, Susan (Nov. 1998), "The Major Outer Protein of Chlamydia Psittaci Functions as a Porin–like Ion Channel." *Infection and Immunity*, pp. 5202–5207.
Ellington et al. (1990) "In vitro selection of RNA molecules that bind specific ligands." *Nature*, vol. 346:818–22.
Gold et al. (1995) "Diversity of Oligonucleotide Functions." *Annu. Rev. Biochem.*, vol. 64:763–97.
Tuerk et al. (1990) "Systematic Evolution of Ligands by Exponential Enrichment: RNA Ligands to Bacteriophage T5 DNA Polymerase." *Science*, vol. 249(4968):505–510.
Yang et al. (1998) "DNA ligands that bind tightly and selectively to cellobiose." *Proc. Natl. Acad. Sci. USA*, vol. 95:5462–5467.

* cited by examiner

*Primary Examiner*—David Guzo
*Assistant Examiner*—Quang Nguyen
(74) *Attorney, Agent, or Firm*—Pamela J. Sherwood; Bozicevic, Field & Francis LLP

(57) ABSTRACT

Infectious human cytomegalovirus (HCMV) were isolated in vitro from a pool of randomized sequences after sixteen or 21 cycles of selection and amplification. The ligands characterized exhibited high HCMV-binding affinity in vitro and effectively inhibited viral infection in tissue culture. Several ligands blocked viral entry. Their antiviral activity was also specific as the ligands only reacted with strains of HCMV, but not with the related herpes simplex virus 1 and human cells. Moreover, the ligands recognize several different epitopes. Thus, RNA ligands can function to bind to a human virus and block viral infection. The screening method may utilize the novel features of binding to intact infectious virus, partitioning the bound polynucleotides from unbound by passing through a porous filter, and enhancing the release of bound polynucleotides by treatment with protease.

8 Claims, 10 Drawing Sheets

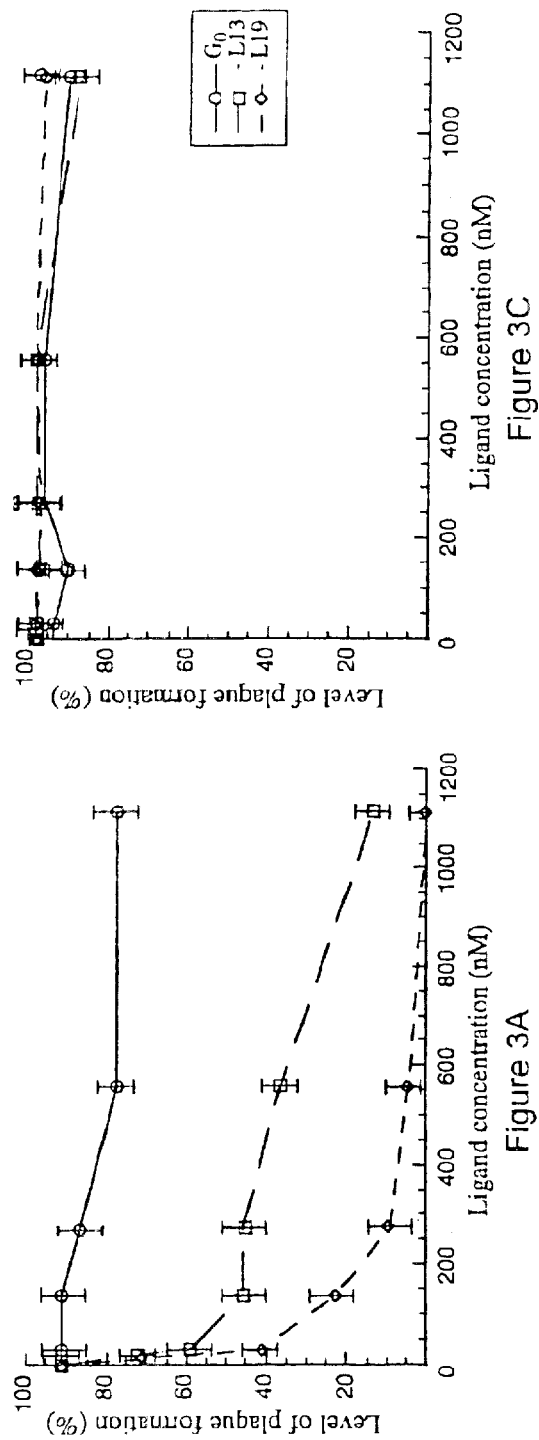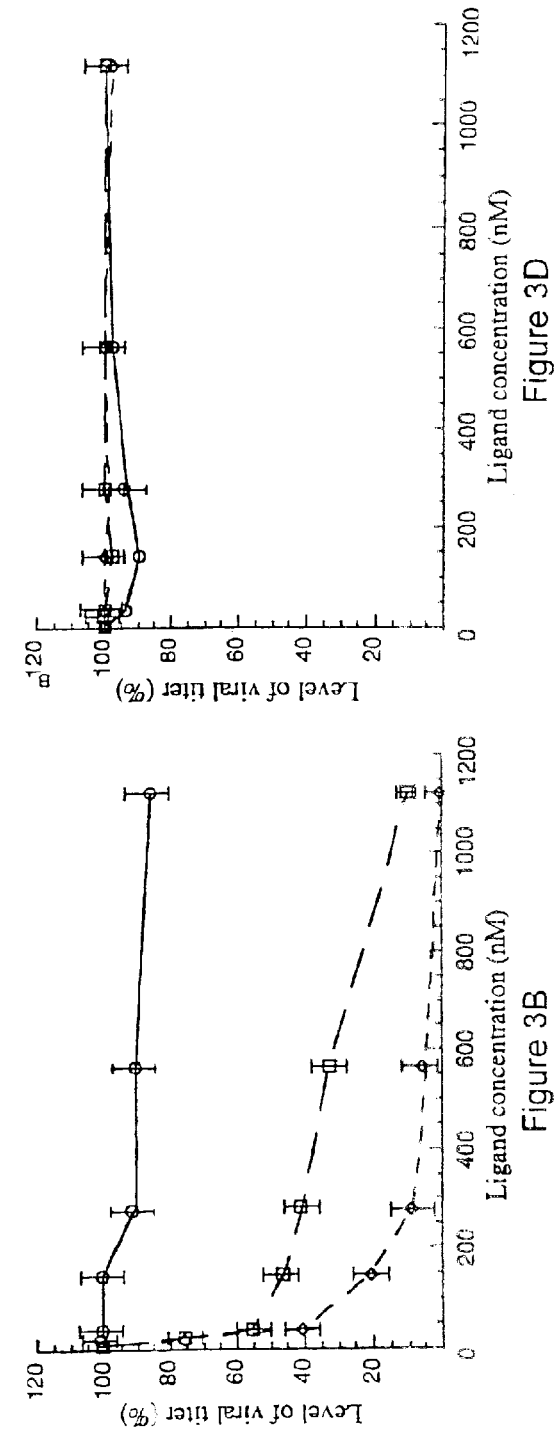

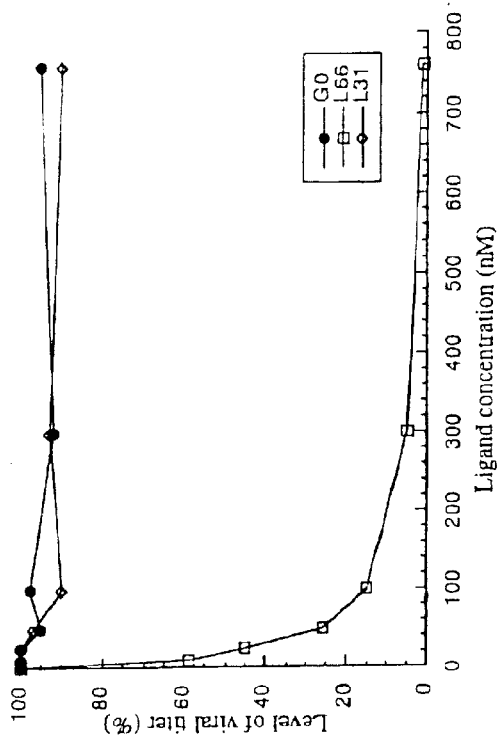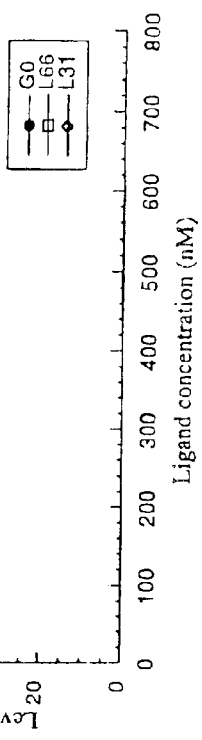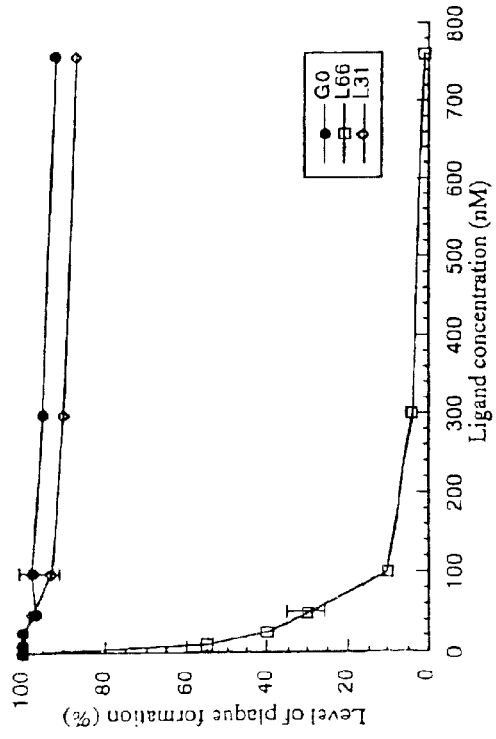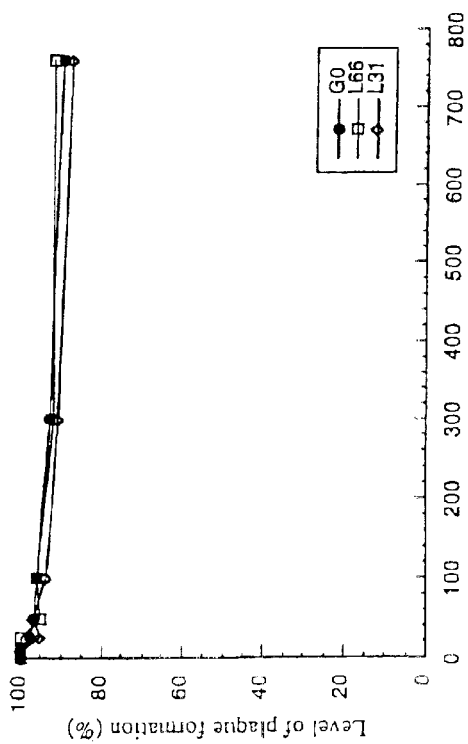
Figure 9A
Figure 9B
Figure 9C
Figure 9D

POLYNUCLEOTIDE LIGANDS AS ANTI-VIRAL AGENTS

RELATED PATENTS AND APPLICATIONS

This application claims priority to U.S. Provisional Application 60/167,509, filed Nov. 24, 1999, now expired.

BACKGROUND

While the development of antibiotics has revolutionized medicine, effective treatment of viral infections has proved to be more elusive. In particular, chronic infections, such as those associated with retroviruses and herpesviruses, are considerable health problems, particularly for immunocompromised patients.

The genus of human herpesviruses (HHV) include cytomegalovirus (CMV, also referred to as HHV-5); herpes simplex virus (HSV-1); human herpes virus (HHV-2); herpes varicella-zoster (HHV-3) which occurs clinically as either an acute form known as chickenpox or a chronic form termed shingles; Epstein-Barr virus (HHV4); human B cell lymphotrophic virus (HHV-6); HHV-7, a T cell lymphotrophic virus; and HHV-8, which is associated with Kaposi's Sarcoma.

Infection with herpes viruses leads to a lifelong association of virus and host. Following a primary infection, virus may be shed for a number of years. With CMV and EBV, infection in otherwise healthy individuals is often asymptomatic, and a significant proportion of the adult population harbor these viruses in latent form. In immunocompromised individuals, such as chemotherapy patients, organ transplant patients and in particular AIDS sufferers, latent CMV can be re-activated resulting in microcephaly, hepatosplenomegaly, jaundice, convulsive seizures which may cause mental retardation, mononucleosis, retinitis and even death. In AIDS patients, CMV is a predominant cause of morbidity.

A variety of drugs have been developed to treat herpesvirus infections, including naturally occurring proteins and synthetic nucleoside analogs. For example, the natural anti-viral protein, interferon, has been used in the treatment of herpesvirus infections, as have the nucleoside analogs, cytosine-arabinoside, adenine-arabinoside, iodoxyuridine and acyclovir, which is presently the treatment of choice for herpes simplex type I infection. Unfortunately not all of these are effective to treat CMV infection. And, drugs currently used to treat CMV infection, such as ganciclovir (9-(1,3-dihydroxy-2-propoxy)methylguanine) and foscarnet (phosphonoformic acid), have side effects and safety issues.

In vitro selection or SELEX (systematic evolution of ligands by exponential enrichment) procedures (Ellington and Szostak (1990) *Nature* 346:818–22; Tuerk and Gold (1990) *Science* 249:505–10) has been used to isolate oligonucleotide molecules with high affinity to a wide variety of low molecular weight targets and large complexes (Yang et al. (1998) *P.N.A.S.* 95:5462–7; Gold et al. (1995) *Ann. Rev. Biochem.* 64:763–97.). In these procedures, single-stranded oligonucleotide molecules that exhibited the highest affinity to a target are selected from a pool of randomized sequences by reiterative cycles of selection and amplification.

However, little is known about whether RNA ligands can bind to a human virus and block its infection. Compared to monoclonal and polyclonal antibodies, nucleic acid-based ligands possess similar activity (high affinity and specificity) as well as other unique features (Gold et al. (1995), supra.) However, the nature of the interactions between these ligands and their protein targets might be different from those between antibodies and the same targets. Therefore, targets that are not considered immunogenic to antibodies may be tightly bound by RNA ligands. The development of novel anti-viral reagents is of great interest.

Relevant Literature

The systematic evolution of ligands by exponential enrichment was first described by Tuerk and Gold (1990) *Science* 249(4968):505–10; and is also described in U.S. Pat. No. 5,496,938, entitled "Methods of Producing Nucleic Acid Ligands".

Modifications of the SELEX procedure using modified nucleotides are described in U.S. Pat. No. 5,958,691, Pieken et al., Sep. 28, 1999. Such ligands enrich the chemical diversity of the candidate mixture for the SELEX process. Specific examples are provided of nucleic acids containing nucleotides modified at the 2'- and 5-position. Specific 2-OH and 2'-NH$_2$ modified RNA ligands to thrombin are described.

SUMMARY OF THE INVENTION

Compositions and methods are provided for the treatment of viral infection by administering polynucleotides that bind to the virus and decrease infection. The use of ribonuclease-resistant polynucleotides is preferred. Of particular interest is the treatment of infections caused by herpesviruses, including human cytomegalovirus (HCMV). Polynucleotide ligands specific for HCMV infection are provided.

In one embodiment of the invention, the virus is a herpes virus and an anti-viral agent of this invention is administered to a patient in need thereof to treat viral-associated conditions such as lesions or herpetic ulcers. In particular, a herpesvirus of interest is cytomegalovirus (CMV), and an anti-viral agent of this invention is administered to a patient in need thereof to treat CMV-associated conditions such as pneumonia, gastroenteritis and chorioretinitis. In a further embodiment, a pharmaceutical composition is provided containing one or more anti-viral agents of this invention in combination with a pharmaceutically or prophylactically acceptable carrier or diluent.

BRIEF DESCRIPTION OF THE DRAWINGS

FIG. 1A. Schematic representation of the evolution in vitro procedures to select RNA analogs that bind to HCMV particles. The pool of DNA molecules contained a randomized sequence of 40 nucleotides indicated as N. (FIG. 1B) increased binding affinity of the populations of RNA analogs during selection from cycle 0 to cycle 16. Binding assays were carried out with different concentrations of virus and a trace amount (<100 fmol) of ligands. The values of binding affinity were calculated by dividing the percentage of bound ligands with the concentration of HCMV used ($\mu$g protein/ml). Each point represents the mean of duplicate measurements.

(FIG. 2A). 1 nM of different selected ligands were allowed to bind to different concentrations of HCMV particles. The values for the percentage of binding represent the mean of triplicate experiments and are not significantly different when 0.1 nM–5 nM of ligands were used in the binding assays. (FIG. 2B). 1 nM of radiolabeled L13 was allowed to bind to 1×10$^5$ pfu/ml (about 30 $\mu$g viral protein/ml) HCMV in the presence of different concentrations of unlabeled L13, L19, G$_0$, and tRNA$^{ser}$. The level of binding of L13 was calculated as the ratio of the percentage of bound radiolabeled L13 in the presence of other ligands over that obtained in the absence of these ligands. The values are the means of triplicate experiments. A value of 100% indicated that there was no competition between the binding of L13 and the other ligand molecules to HCMV.

FIG. 3. FIGS. 3A–3D. Effect of the ligands on plaque formation (FIG. 3A and FIG. 3C) and particle production (FIG. 3B and FIG. 3D). $1\times10^5$ pfu/ml HCMV (AD169) or HSV-1 (F) was incubated in DMEM media alone or in the presence of different concentrations of $G_0$, L13, L19 at 37° C. for 15 mins before used to infect HFFs at MOI of 0.005 (for plaque assay) or 0.3 (for titer assay). The levels of viral titer and plaque formation were calculated as the ratio of the titers and plaque numbers assayed from experiments with HCMV incubated in the presence of the ligands over those from experiments with HCMV incubated in DMEM alone, respectively. The values are the means of triplicate experiments.

FIGS. 9A–9D. Effect of the ligands on plaque formation (A and C) and particle production (B and D) of HCMV (AD169) (A and B) and herpes simplex virus 1 (F) (C and D) in human foreskin fibroblasts (HFFs). $1\times10^5$ PFU/ml HCMV (AD169) or HSV-1 (F) was incubated in DMEM media alone or in the presence of different concentrations of $G_0$, L31, L66 at 37° C. for 15 mins before being used to infect HFFs at MOI of 0.02 (for plaque assay) or 0.5 (for titer assay). The levels of viral titer and plaque formation were calculated as the ratio of the titers and plaque numbers assayed from experiments with HCMV incubated in the presence of the ligands over those from experiments with HCMV incubated in DMEM alone, respectively. The values are the means from triplicate experiments.

DETAILED DESCRIPTION OF THE PREFERRED EMBODIMENTS

Figure 1A:
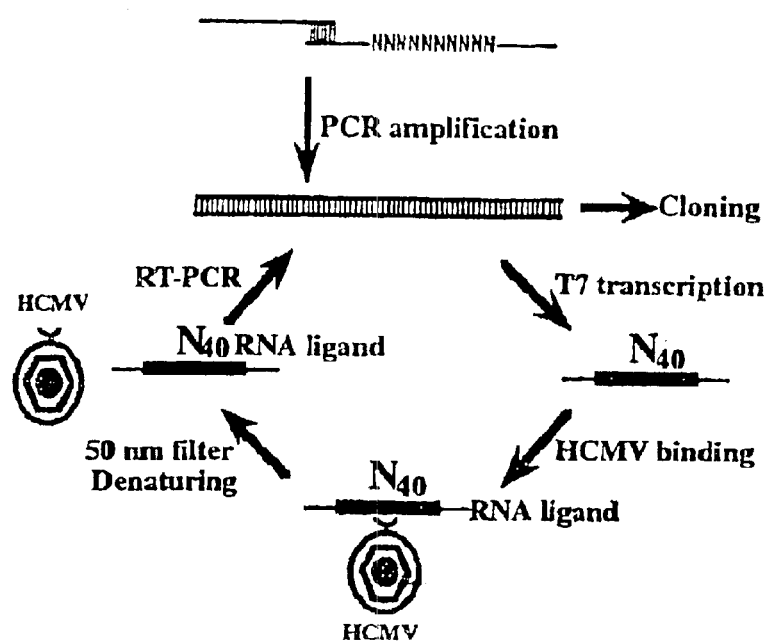
FIGS. 1A–1B.
Figure 1B:
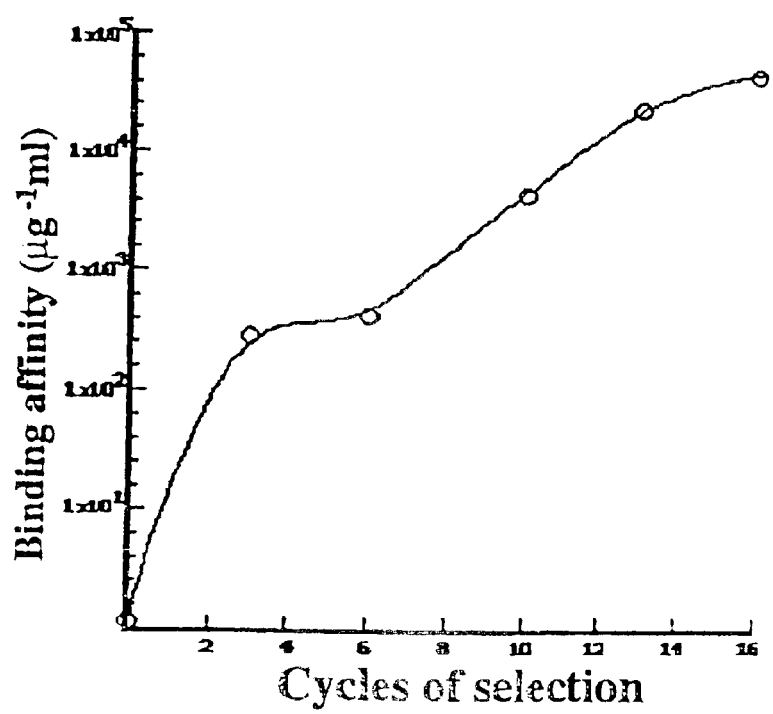

Using methods of systematic evolution of ligands by exponential enrichment (SELEX) polynucleotide ligands having antiviral activity are isolated. The ligands are selected by binding to whole virus, or to fragments derived therefrom. Preferably the ligands comprise nucleotides that provide for enhanced resistance to RNAse, e.g. comprising chemically modified ribonucleotides. In one embodiment of the invention, the ligands comprise 2'-amino-modified pyrimidine ribonucleotides. The ligands are used in antiviral therapies, particularly for the treatment of herpesvirus infections, e.g. primary or chronic infections with human cytomegalovirus (HCMV).

Before the present anti-viral compositions and methods are described, it is to be understood that this invention is not limited to the particular embodiments described, as such methods, devices, and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, and reference to "the method of delivery" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the specific methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed Definitions Anti-viral polynucleotide ligand: as used herein, are nucleic acids that bind to a virus, and act to decrease the infection of target cells by the virus. The anti-viral effect may interfere at a number of different point in the infection process, including binding of virus to a cellular receptor, entry of virus into cell, initiation of replication, release of viral particles, etc.

The polynucleotide ligands are isolated by the SELEX procedure, as described below, and have a high affinity, specific binding to the targeted virus or fragment thereof. The active binding portion of the molecule is usually at least about 10 nucleotides in length, more usually at least about 15 nucleotides in length, and may be much as 30 to 40 nucleotides in length. The molecules are usually not more than about 100 nucleotides in length. In addition to the portion of the polynucleotide involved in binding, the molecule may comprise sequences ligated to one or both of the 3' and 5' flanking regions of the polynucleotide. Such flanking sequences may serve a variety of functions, e.g. to aid in the SELEX procedure, for cloning purposes, as a tag for detection, etc.

The sequence of the provided ligands may be mutated to generate targeted changes. The nucleotide sequence or product of such a mutation will be substantially similar to the sequences provided herein, i.e. will differ by at least one nucleotide or amino acid, respectively, and may differ by at least two but not more than about ten nucleotides or amino acids. The sequence changes may be substitutions, insertions or deletions.

otides of the invention act by binding to proteins, e.g. envelope proteins, or other macromolecules on the surface of the viral envelope.

Specific examples of anti-viral ligands for human cytomegalovirus are provided in Tables 1 and 2.

TABLE 1

RNA Ligand Sequences

| SEQ ID NO. | Clone | Sequence |
|---|---|---|
| Set I | | |
| SEQ ID NO:1 | 8 | TTACGGTCAC CTTACCCCTG GGTGTGCTCT TCCCGGTGGG |
| SEQ ID NO:2 | 13 | TTACGGTCAC CTTACCCCTG GGTGTGCTCT TCCCGGTGGG |
| SEQ ID NO:3 | 14 | TCACAGTCAC CTTACCCCTG GGTGTGCTCT TCCCGGTGGG |
| SEQ ID NO:4 | 55 | TCACAGTCAC CTTACCCCTG GGTGTGCTCT TCCCGGTGGG |
| SEQ ID NO:5 | 63 | TTACGGTCAC CTTACCCCTG GGTGTGCTCT TCCCGGTGGG |
| SEQ ID NO:6 | 70 | TCACAGTCAC CTTACCCCTG GGTGTGCTCT TCCCGGTGGG |
| Set II | | |
| SEQ ID NO:7 | 1 | GCGAATTAAC ACATCGGGCC CATCGTCCGA GGTGCGTGGG |
| SEQ ID NO:8 | 57 | GCGAATTAAC ACATCGGGCC CATCGTCCGA GGTGCGTGGG |
| SEQ ID NO:9 | 69 | GCGAATTAAC ACATCGGGCC CATCGTCCGA GGTGCGTGGG |
| Set III | | |
| SEQ ID NO:10 | 17 | CATCTCTCCT CACCATACCT CCACTTCCTG GGCTCGTGGG |
| SEQ ID NO:11 | 21 | CATCTCTCCT CACCATACCT CCACTTCCTG GGCTCGTGGG |
| Set IV | | |
| SEQ ID NO:12 | 19 | CTCGAGCCAC CCCATAACCC TCAATACTCC AGGGATTGGG |
| SEQ ID NO:13 | 53 | CTCGAGCCAC CCCATAACCC TCAATACTCC AGGGATTGGG |
| Set V | | |
| SEQ ID NO:14 | 11 | CATCACTTGA CCCTACTCTA CCTGGGCTGG ACTGGGTGGG |
| SEQ ID NO:15 | 58 | CTATTTCCCA CCCATATCCC CTTGGGCCCT TGGGTGTGGG |
| SEQ ID NO:16 | 49 | CTATATCCAC CCXATATCCC CTTXXCCCCT TGCGTGTGGG |
| Set VI | | |
| SEQ ID NO:17 | 2 | GCACGACTCT CACTCAAGGG TCGATGCAGG CGTCTGTGGG |
| SEQ ID NO:18 | 3 | ACCTCCATGT CAATATCATC AGTATCAAAA TGGGTGCTGGG |
| SEQ ID NO:19 | 4 | AACCAACTTT TTTCAAACAC TCACTATCTG GGTGTATGGG |
| SEQ ID NO:20 | 5 | CACTCCTTCG CAACACCACT CACCTTGGGA CCTTGGGTGG |
| SEQ ID NO:21 | 9 | GCAGGCACTC TCACTCAAGG GTCGATCAGG CGTCTGTGGG |
| SEQ ID NO:22 | 52 | ATGACTGACT ACACATGCCC CTTAGGGATG TATCTTAGGG |
| SEQ ID NO:23 | 56 | AACCAACCTC TCTCAAACCC TCACTATCGG GTTGTATGGG |
| SEQ ID NO:24 | 61 | ACCAGACGTA TCCACACTCA TTGGGCTTGG TCTCCGTGGG |
| SEQ ID NO:25 | 62 | CTACTCCCTC CCTAACCCTG GGTCCGCTAT ACATGGTGGG |
| SEQ ID NO:26 | 64 | GCCGAATTCA CACATCGGGC CCATCGTCGA GGTGCGTGGG |
| SEQ ID NO:27 | 65 | ACCCCTCTGC CTCACTCCAA TTCAGCGGGC GGTTCGTGGG |
| SEQ ID NO:28 | 18 | GGTCCTACGG ACTTTGGCAC GCAATCACTA GGTGTTTGGG |

TABLE 2

| Ligands | clone | 40 nt randomized sequence |
|---|---|---|
| Set VII | | |
| SEQ ID NO:36 | 66 | TGTGGGTCGT GTTAAGCTTCGGGCTTCGCG CAAATCTGGG |
| SEQ ID NO:37 | 32 | TCTGGGTCGT ATTAAGCTTC GGGCTTCGCG CAAATCTGGG |
| Set VIII | | |
| SEQ ID NO:38 | 31 | CAGTACCGGC CACATTCCCC ATCATCATAC ATGGGTGGGG |
| Set IX | | |
| SEQ ID NO:39 | 33 | CTACTAGCGA GCACGCGCTC ATCGCGCCAG TGCCATTGGG |
| SEQ ID NO:40 | 39 | CGAGACTAGC GAGCACGGCT CATCGGTCGA GTGCCAGAAGG |
| SEQ ID NO:41 | 43 | GGCTCATTGA CACAGACTCA TCGTTGGGTC TTGGGTGG |

Unlike anti-sense reagents that act by binding of a polynucleotide to a viral genome or mRNA, the polynucleotides isolated by the present methods are generally not complementary to a viral genetic sequence. Rather, the polynucle- These ligands fall into roughly nine groups, based on sequence similarities. At least one ligand from each group was tested, and found to bind to HCMV viral particles at high affinity. A comparison of ligands from two different groups, for example (set I and set IV; SEQ ID NO:2 and SEQ ID NO:12) showed that the affinity of one was not significantly affected by the presence of the other, demonstrating that these two ligands recognize different viral epitopes or targets.

The ligands of interest show significant antiviral activity, e.g. as evidenced by reduction of viral plaque formation in cells infected with viruses; reduction in viral yield; etc. The ligands may be combined to obtain an additive or synergistic effect. Preferably the ligands have a high affinity for different strains of the virus target, e.g. isolates of HCMV, but low affinity for non-targeted virus. Usually the difference in affinity between a targeted and non-targeted virus (for example CMV vs. HSV) is at least about 10 fold, more usually at least about $10^2$-fold, and may be as much as $10^3$ fold or more.

RNAse resistant polynucleotide: Preferred ligands comprise nucleotides that provide for RNAse resistance. By RNAse resistant, it is meant that the molecule is not significantly degraded after overnight incubation in serum, under which conditions native RNA is degraded. The major degradation of oligoribonucleotides in serum proceeds through pyrimidine-specific endonuclease (Pieken et al. (1990) *Science* 253:314). Some nucleotides are naturally RNAse resistant, e.g. deoxyribonucleotides. Other may be chemically modified from the native nucleotide structure, in order to increase their intracellular stability and binding affinity. A number of nucleotide modifications have been described in the art, where the chemistry of the phosphodiester backbone, sugars or heterocyclic bases is altered.

In a preferred embodiment, the heterocyclic bases or sugars are altered, but the phosphodiester backbone has a chemistry compatible with naturally occurring polymerases. Modified nucleotide bases include substitutions at the 2' or 5 position in pyrimidine bases, and the 2' or 8 position substitutions in purine bases.

The resistance of 2'-amino, 2'-deoxy pyrimidine homopolymers to degradation by pancreatic ribonuclease (RNAse A) has been reported. Both poly (2'-amino, 2'-deoxyuridine) and poly (2'-amino, 2'-deoxycytidine) are essentially completely stable towards RNAse A degradation, and are reported to have a stability in rabbit serum that is 1200-fold increased compared to unmodified oligoribonucleotides (Pieken et al. (1990) supra). As expected, these polymers are readily degraded by snake venom phosphodiesterase, an enzyme that catalyzes water-hydrolysis of the phosphodiester backbone. In this embodiment of the invention, usually at least about 50% of the pyrimidines present in the polynucleotide are thus modified, more usually at least about 75%, and may be about 90% or substantially all of the pyrimidines present.

Other oligonucleotides modified so as to exhibit resistance to nucleases are known in the art, e.g. 2'-deoxy-2'-fluoroguanosine; 2'-deoxy-2'-fluoroadenine residue; 2'-chloro or bromo substituents; 2'-OCH$_3$, etc. The 2'-amino, 2'-deoxy pyrimidine synthesis is described in U.S. Pat. No. 3,755,295, issued Aug. 28, 1973.

Specific nucleotide analogs modified at the 5 and 2' positions include 5-(3-aminoallyl) uridine triphosphate (5-AA-UTP), 5-(3-aminoallyl) deoxyuridine triphosphate (5-AA-dUTP), 5-fluorescein-12-uridine triphosphate (5-F-12-UTP), 5-digoxygenin-11-uridine triphosphate (5-Dig-11-UTP), 5-bromouridine triphosphate (5-Br-UTP), 2'-amino-uridine triphosphate (2'-NH.sub.2-UTP) and 2'-amino-cytidine triphosphate (2'-NH.sub.2-CTP), 2'-fluoro-cytidine triphosphate (2'-F-CTP), and 2'-fluoro-uridine triphosphate (2'-F-UTP).

Sugar modifications are also used to enhance stability and affinity. The α-anomer of deoxyribose may be used, where the base is inverted with respect to the natural β-anomer. The 2[]-OH of the ribose sugar may be altered to form 2[]-O-methyl or 2[]-O-allyl sugars, which provides resistance to degradation without comprising affinity. The stability of oligoribonucleotides against endonuclease degradation may be achieved by replacement of the 2'-OH group of the ribose moiety with an alternate substituent such as an amino group or a fluoro group (Pieken et al. (1991) supra). Both 2'-amino and 2'-fluoro nucleoside 5-triphosphates are substrates for T7 RNA polymerase (Aurup et al. (1992) *Biochemistry* 31:9636–9641.

Viral SELEX (Systematic evolution of ligands by exponential enrichment): is a procedure for isolating polynucleotides having a high affinity for a virus binding target, where repeated rounds of binding to the virus target, washing off unbound polynucleotides, and amplification of the bound polynucleotides provides for a high affinity polynucleotide ligand. In the present application, the binding target is a virus, viral particle, or fragment of a virus. Usually at least about 5 rounds of SELEX selection are performed, more usually at least about 10 rounds of selection, and may use as many as 20 rounds of selection or more.

The rounds of selection are performed as follows. A candidate mixture of nucleic acids of differing sequence is prepared. The candidate mixture generally includes regions of fixed sequences, e.g. regions complementary to amplification primers; and regions of randomized sequences. The fixed sequence regions are selected for various purposes, e.g. to assist in the amplification steps; mimic a sequence known to bind to the target; enhance the concentration of a given structural arrangement of the nucleic acids in the candidate mixture; and the like. The randomized sequences can be totally randomized or only partially randomized. See, for example, U.S. Pat. No. 5,475,096 for a description of randomized pools of polynucleotides.

The virus binding target is contacted with a pool of polynucleotides under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target.

The nucleic acids with the highest affinity for the target are partitioned from those nucleic acids with lesser affinity to the target. Because only an extremely small number of sequences corresponding to the highest affinity nucleic acids exist in the candidate mixture, it is generally desirable to set the partitioning criteria so that a significant amount of the nucleic acids in the candidate mixture, generally from about 5–10% are retained during partitioning. This partitioning may use any one of a variety of techniques to partition the unbound material from the bound.

Partitioning can be accomplished by various methods known in the art. In a preferred embodiment partitioning utilizes a filter that achieves size separation of the bound and unbound components, e.g. filters having a pore size sufficient to retain viral particles but to pass through unbound nucleic acids. For example, a porous filter may have pores of from about 10 nm to 100 nm, usually from about 20 nm to about 60 nm, and may be about 40 to 50 nm, depending on the size of particle that will be excluded. The partitioning may be further enhanced by treating the bound material with a broad specificity protease, e.g. trypsin, dispase-collagenase, proteinase K, etc. in order to improve release of the nucleic acid from the retained material.

Nucleic acid-protein pairs may also be bound to nitrocellulose filters while unbound nucleic acids are not. Columns that specifically retain ligand-target pairs can be used for partitioning. Liquid-liquid partition can also be used as well as filtration gel retardation, and density gradient centrifugation. The choice of partitioning method will depend on properties of the target and of the ligand-target pairs and can be made according to principles and properties known to those of ordinary skill in the art.

In a preferred embodiment, the binding target is bound to the surface of an insoluble support either before or after binding to the pool of polynucleotides. The support binding may use any convenient means, depending upon the nature of the surface, covalently or non-covalently, preferably non-covalently. The insoluble supports may be any compositions to which virus can be bound, which is readily separated from soluble material; and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. For example, oligonucleotides bound to proteins can be effectively separated from the unbound species by filtration through nitrocellulose membrane filters (Tuerk & Gold (1990) supra).

After incubation, the insoluble support is generally washed of non-bound components. One or more washes may be employed, with sufficient volume to thoroughly wash non-specifically bound polynucleotides present in the sample.

Those nucleic acids selected during partitioning as having the relatively higher affinity to the target are then separated from the virus binding target, and amplified to create a new candidate mixture that is enriched in nucleic acids having a relatively higher affinity for the target. Amplifying may use any process or combination of process steps that increases the amount or number of copies of a molecule or class of molecules, e.g. RT-PCR coupled with transcription to obtain RNA molecules having the same sequences as the selected RNAs. Any reaction or combination of reactions known in the art can be used as appropriate, including direct DNA replication, direct RNA amplification and the like, as will be recognized by those skilled in the art. The amplification method should result in the proportions of the amplified mixture being essentially representative of the proportions of different sequences in the initial mixture.

By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

Virus target: as used herein, the term. "virus target" is used to generally refer to a complete virus particle or virion, a nucleocapsid, capsid, or macromolecule from the virus, which may be a lipid, polysaccharide, protein, etc., usually an envelope or capsid protein. Viruses are infectious agents, usually comprising only one kind of nucleic acid as their genome. The nucleic acid is encased in a protein shell of capsid proteins, which forms the nucleocapsid particle. The nucleocapsid may be further surrounded by a lipid containing membrane, into which are typically inserted envelope proteins.

Viruses may be classified according to their genome composition. DNA viruses include parvoviruses, papovaviruses, adenoviruses, herpesviruses, poxviruses and hepanaviruses. RNA containing viruses include caliciviruses, reoviruses, arboviruses, togaviruses, flaviviruses, arenoviruses, coronaviruses, retroviruses, bunyaviruses, orthomyxoviruses, paramyxoviruses, and rhabdoviruses.

Herpesvirus: is a class of viruses containing several important human pathogens. An important property of herpesviruses is their ability to establish life-long persistant infection of the host, and to undergo periodic reactivation. Their frequent reactivation in immunosuppressed patients frequently causes health problems. The reactivated infection may be clinically very different from the disease caused by primary infection.

There are eight herpesviruses known to infect humans: herpes simplex viruses 1 and 2; varicella-zoster virus, cytomegalovirus, Epstein-Barr virus, human herpesvirus 6 and 7, and Kaposi's Sarcoma associated herpesvirus (HHV-8). All herpesviruses have a core of double-stranded DNA surrounded by a protein coat having icosahedral symmetry. The nucleocapsid is surrounded by an envelope that is derived from the nuclear membrane of the host cell, and contains viral glycoprotein spikes.

Pharmaceutical Formulation: One or more of the anti-viral ligands may be combined with a pharmaceutically acceptable carrier, which term includes any and all solvents, dispersion media, coatings, anti-oxidant, isotonic and absorption delaying agents and the like. The use of such media and agents for pharmaceutically active substances is well known in the art. Except insofar as any conventional media or agent is incompatible with the active ingredient, its use in the therapeutic compositions and methods described herein is contemplated. Supplementary active ingredients can also be incorporated into the compositions.

The formulation may be prepared for use in various methods for administration. The formulation may be given orally, by inhalation, or may be injected, e.g. intravascular, intralesion, subcutaneous, intraperitoneal, intramuscular, etc.

The dosage of the therapeutic formulation will vary widely, depending upon the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc. to maintain an effective dosage level. In some cases, oral administration will require a higher dose than if administered intravenously.

The anti-viral ligands can be incorporated into a variety of formulations for therapeutic administration. More particularly, the complexes can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the anti-viral ligands can be achieved in various ways. The anti-viral ligands may be systemic after administration or may be localized by the use of an implant that acts to retain the active dose at the site of implantation.

For use in the subject methods, the anti-viral ligands may be formulated with other pharmaceutically active agents, particularly other anti-viral or antibiotic agents.

Dosages may vary with the mode of administration and the particular compound chosen. In addition, the dosage may vary with the particular patient under treatment. The dosage of the compound used in the treatment will vary, depending on viral load, the weight of the patient, the relative efficacy of the compound and the judgment of the treating physician. Such therapy may extend for several weeks or months, in an intermittent or uninterrupted manner.

Methods of Use

The provided methods of viral SELEX are used to isolate polynucleotides that bind to virus targets. The ability of such polynucleotides to block viral infection may then be assessed in biological assays of viral infection and replication, as known in the art, and as described in the examples. Once the sequence of an anti-viral polynucleotide is determined, the polynucleotide may be synthesized in vitro, or produced by conventional recombinant methods, by PCR, etc. The polynucleotide may be synthesized from native nucleotide monomers, or from analogs, particularly RNAse resistant analogs.

For treatment or prevention of viral infection, the polynucleotide is formulated in a carrier appropriate for the route of administration. An effective dose for the treatment of an on-going, or reactivation of a latent infection, is the amount of active compound required to slow the progression of viral replication or reduce viral load from that which would otherwise occur without administration of said compound. Or, it is an amount of active compound required to slow the progression or reduce the intensity of symptoms resulting from virus infection or elimination thereof. For in vitro use, e.g. to control CMV infection in cultured cells, the effective amount of anti-viral polynucleotide is that which yields a concentration in the medium sufficient to inhibit viral replication in the cultured host.

In one embodiment of the invention, the virus infection is infection with CMV. Where term "cytomegalovirus" is meant to encompass laboratory and other cytomegalovirus strains that infect humans, as well as cytomegalovirus strains that infect other mammals including mice, rats, cats, dogs and horses as well as livestock such as sheep and cattle.

Compositions that are effective to control CMV infection have the property of slowing, interrupting, arresting or stopping replication of at least one CMV strain, as determined by a cell culture assay used conventionally in the art, such as the well established plaque reduction assay. For example, the anti-viral nature of a given compound may be indicated by a statistically significant reduction in plaque number and/or size, relative to an untreated control.

For clinical use, the reduction in viral load may be determined by assaying virus titer in samples of biological fluid, such as blood and urine, obtained from the patient before and after treatment. Candidates for treatment are those patients in an immunocompromised condition, including neonates, AIDS patients, patients undergoing cancer chemotherapy and organ and tissue transplant patients undergoing tissue rejection therapy. Clinically effective doses of the anti-CMV peptides are determined using clinical trial protocols established for other anti-CMV drugs, such as ganciclovir.

EXPERIMENTAL

Example 1

In Vitro Selection of Novel RNA Ligands that Bind Human Cytomegalovirus and Block Viral Infection Isolation of ribonuclease-resistant RNA analogs that exhibit high affinity to HCMV. Procedures to select RNA ligands involved the synthesis of RNA analog molecules that contained 2'-amino-modified pyrimidine nucleotides, selection experiments in vitro for the modified RNA molecules that bind to infectious HCMV, and purification and amplification of the selected sequences. The viral particles were isolated from HCMV-infected human foreskin fibroblasts (HFFs) by gradient ultracentrifugation as described previously. The infectivity of the purified HCMV was evaluated by titering the particles in human fibroblasts and the intactness of their structures was examined first by obtaining negative staining images with a conventional transmission electron microscope and further confirmed by electron cryomicroscopy. Only those HCMV preparations that exhibited the highest titer ($>5 \times 10^8$ PFU/ml) and most intact particles were used for the selection.

In order to increase the stability of the selected molecules, RNA analog molecules that contained 2' amino-modified pyrimidines were synthesized in vitro by T7 RNA polymerase in the presence of the modified nucleotide triphosphates. RNA molecules with 2'-amino pyrimidines have been previously shown to be very stable in the presence of bovine and human serum and resistant to degradation by RNases. In our experiments, most of the 2'-amino modified RNA molecules remained intact, even after a 24 hour incubation with HCMV, while the unmodified RNA molecules were totally degraded in 1 hour. Accordingly, the 2'-amino-substituted RNA molecules were used in the selection and were synthesized in vitro from a pool of DNA molecules that contained 40 randomized positions. Then, these RNA analog molecules were allowed to bind to HCMV, and the mixtures passed through a 50 nm pore-size filter. Because HCMV is more than 200 nm in diameter, the bound ligands along with the viral particles were retained on the filter and subsequently purified while those unbound passed through cDNA molecules were synthesized and amplified from the purified ligands and subsequently served as the templates for the synthesis of the ligand molecules to be used in the next round of selection (FIG. 1A). This process was repeated sixteen times and the binding affinity (measured as the value of binding percentage/viral protein concentration) of the ligand population after sixteen cycles was higher than that of the initial randomized RNA ($G_0$) by a factor of more than $5 \times 10^4$.

Sequencing analyses and biochemical characterization of the selected ligands. Twenty eight sequences coding for the ligands after sixteen rounds of selection were cloned and characterized (Table 1). These ligands were divided into six sets based on their primary nucleotide sequences. In sets II, III, and IV, the individual sequences were identical to each other within the same set. Meanwhile, each sequence in sets I and V either had the same sequence or extensive homology to other sequences of the same set. In contrast, the twelve sequences in set VI are unrelated to each other and to any other sets. The diversity of the selected sequences is consistent with the notion that these ligands might have been selected to recognize different epitopes or targets on the surface of HCMV. These selected sequences were not found in the genomic sequence of HCMV. This observation indicated that the selected sequences were neither derived from viral genomic sequence nor antisense to the HCMV sequences.

Figure 2A:
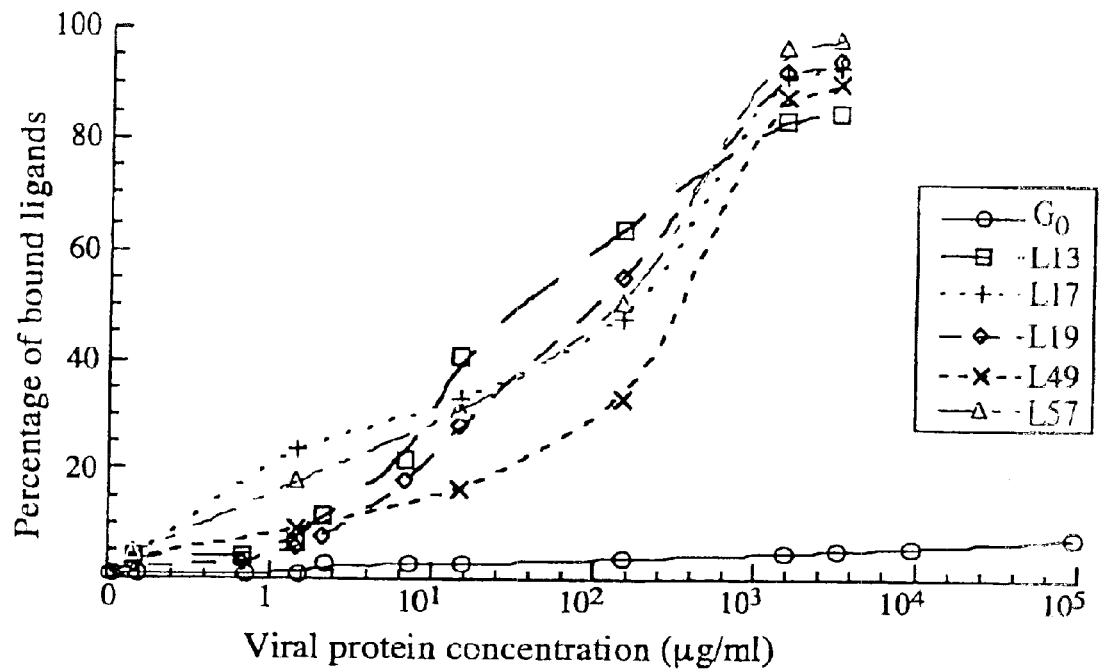
FIGS. 2A–2B Binding affinity of the selected ligands to HCMV.

To analyze the relationship between the sequences of the selected ligands and their capabilities to bind HCMV, five ligands (L13, L17, L49 and L57) were assayed for their binding affinities to the viral particles. These molecules were chosen as representatives of the most abundant selected sequences (Table 1). The protein assays of the infectious HCMV virions indicated that a stock of $1\times10^5$ PFU virus approximately contained 10 μg protein. A trace amount of radiolabeled ligand was incubated with different concentrations (PFU/ml) of purified HCMV in binding buffer III (20 mM Tris, pH 7.5, 100 mM NaCl, 2.5 mM $MgCl_2$) which was used in the selection. All five ligands exhibited high affinity to HCMV. More than 50% of the ligands was bound in the presence of $6\times10^5$ to $4\times10^6$ PFU/ml HCMV (FIG. 2A). In contrast, less than 10% of the $G_0$ molecules remained bound even in the presence of $1\times10^9$ PFU/ml HCMV. The binding affinities of most of these ligands are at least $5\times10^4$ higher than that of the initial randomized pool. Ligands L13, L17, and L19 also exhibited similar binding affinities when binding assays were carried out in Dulbecco's modified Eagle media (DMEM) which resembled the physiological buffer conditions. RNase A digestion of the ligands before binding resulted in the loss of the binding capability of these molecules, indicating that the intact structure of the ligands is essential for HCMV binding.

Figure 2B:
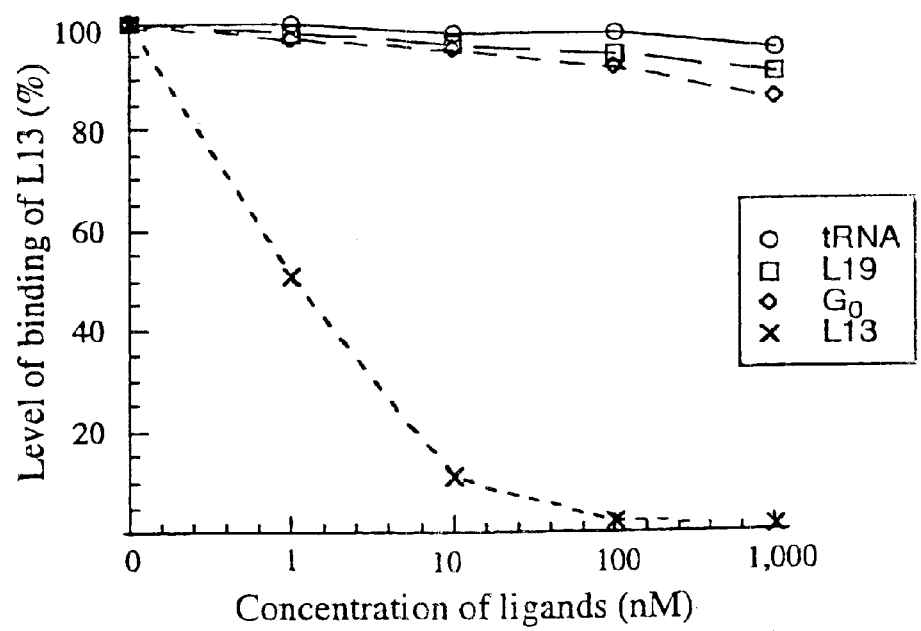

If L13 and L19 recognize different HCMV targets or epitopes, it is expected that these two ligands would not compete for binding to the viral particles. Binding affinity of L13 to HCMV in the presence of different concentrations of L19 (FIG. 2B) and vice versa was determined. As controls, the binding of L13 to HCMV was also assayed in the presence of G0 RNA and $tRNA_{ser}$. The affinity of L13 to HCMV was not significantly affected in the presence of different concentrations of L19, suggesting that these two ligands recognize different viral epitopes or targets (FIG. 2B). Similar results were also observed when the binding of L19 to HCMV was assayed in the presence of L13. As expected, G0 RNA and $tRNA_{ser}$ did not affect the binding of L13 to HCMV.

Antiviral activity of the selected ligands. To determine whether the binding of selected ligands can interfere with the viral replication process and block infection, the purified HCMV particles were first preincubated in vitro with different concentrations of ligands 13, 17, 19, and $G_0$ to allow binding, and then used to infect human foreskin fibroblasts at MOI of 0.001–0.01. After absorption for 2 hours, cells were washed with culture medium (DMEM) to remove residual virus. Then the cells were overlaid with 0.5% agarose and incubated at 37° C., and the number of viral plaques was counted at 10–14 days postinfection. Significant reduction of viral plaque formation was observed in cells infected with viruses that were pretreated with L13 and L19 but not with L17 and G0 (FIG. 3A). The observed level of inhibition of viral plaque formation by L13 and L19 was dependent on the concentrations of the ligands. Results from triplicate experiments indicated that the concentrations ($IC_{50}$) of L13 and L19 for 50% inhibition of plaque formation of $1\times10^5$ PFU/ml HCMV are 125±20 nM and 35±10 nM, respectively (FIG. 3A).

Figure 4:
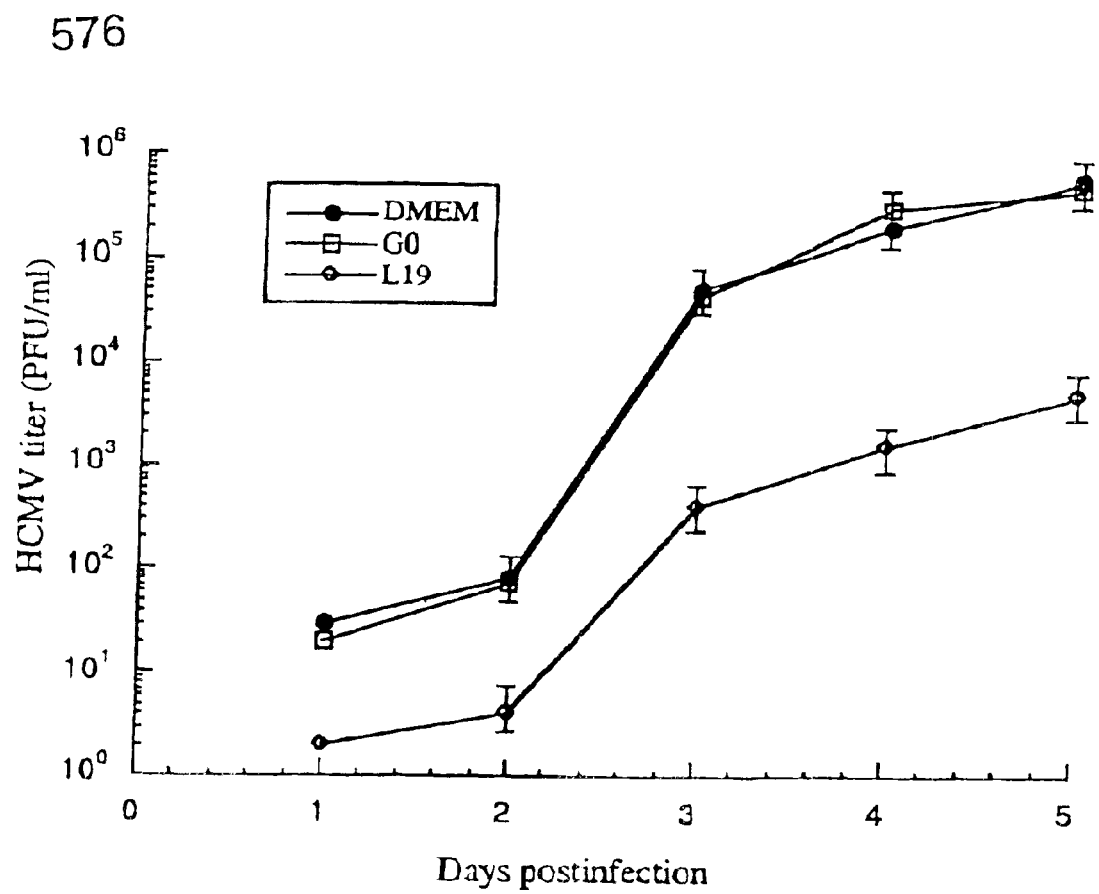
FIG. 4. Growth curve analysis of HCMV in HFFs.

The production of HCMV was also studied to determine whether viral growth is inhibited by binding of the ligands. Cells were first infected with viruses pretreated with L13, L17, L19 and G0, and then further incubated at 37° C. to allow HCMV to grow. Within 36 and 72 hours postinfection, virus stocks were prepared from the infected cultures (cells and culture medium together) and the PFU count was determined by measurement of the viral titer on human fibroblasts. A significant reduction in viral yield was observed in experiments with L13 and L19 but not L17 and G0 (FIG. 3B). The inhibition of viral yield was also ligand dose-dependent, with an $IC_{50}$ for L13 and L19 equal to 100±20 nM and 35±7 nM, respectively. To further determine the inhibitory effects of the ligands on viral growth, cells were infected at a MOI of 1 with HCMV that were treated with 800 nM of $G_0$ and L19, or without the ligands. Virus stocks were prepared from the infected cells at 1 day intervals through 5 days postinfection and the PFU count was determined by measurement of the viral titer in human fibroblasts (FIG. 4). After 3 days postinfection, a reduction of at least 100 fold in viral yield was observed in cells that were infected with HCMV treated with L19 while no significant reduction was found in those treated with G0 (FIG. 4). A reduction of viral plaque formation and viral growth was also observed when HCMV was first bound to L13 and L19 and then washed to remove most of the unbound ligands before being placed on cells.

The binding and antiviral activity of L13 and L19 appeared to be specific for HCMV. In vitro binding affinities of L13 and L19 for HCMV strain AD169, were similar to those for another HCMV strain Towne but were at least $10^4$ fold higher than those for herpes simplex virus 1 (HSV-1) strain F. These ligands also inhibited plaque formation and growth of HCMV (Towne) with a similar level of activity as for the AD169 strain. In contrast, no inhibition was observed when L13 and L19 were used with HSV-1 (FIGS. 3C and D). These results indicate that these two ligands specifically interact with molecules that are found commonly in different HCMV strains but not in HSV-1.

Figure 5:
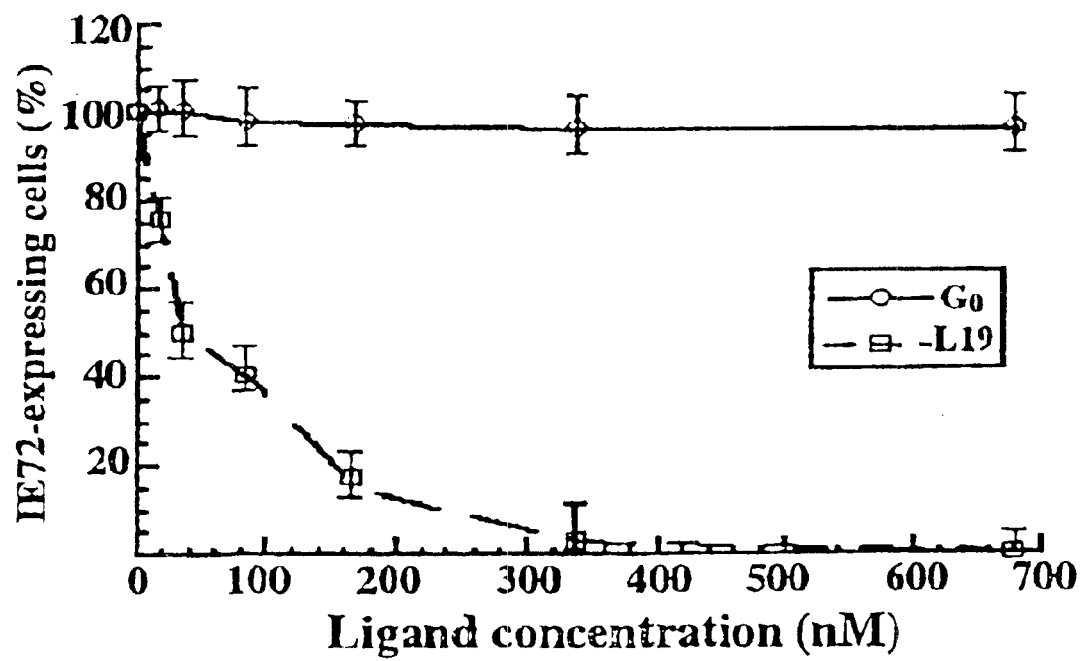
FIG. 5. Schematic representation of the numbers of IE72-expressing cells in the presence of ligands $G_0$ and L19. The numbers of cells that expressed IE72 protein were counted. The values of the percentage shown were calculated by obtaining the ratio of the numbers of IE72-expressing cells infected with viruses treated with the ligands over those without the ligands FIG. 6. Level of intracellular HCMV genomic DNA during early viral infection, Schematic representation of the level of viral DNA assayed from PCR.

Blockage of viral entry by the selected ligands. L19 was chosen as a representative to further study the antiviral mechanism of the selected ligands. Several experiments were carried out to investigate which step(s) of the viral lytic cycle is blocked by L19. First, expression of the viral major immediate-early protein IE72, which is among the first proteins expressed after infection, was determined by Western analyses (FIG. 5A). Human fibroblasts were infected with viruses that were pretreated with culture media (DMEM) alone or in the presence of G0, L19 or nAb, which is a mixture of anti-HCMV glycoprotein B (gB) neutralizing antibodies. The infected cells were harvested at 72 hours postinfection and proteins from the infected cells were separated electrophoretically on SDS-polyacrylamide gels, transferred to a nitrocellulose membrane, and finally stained with anti-IE72 monoclonal antibody mAb1203 (FIG. 5A). The IE72 expression was barely detected in cells infected with HCMV pretreated with 680 nM of L19 and 200 μg/ml of anti-HCMV gB neutralizing antibodies nAb (FIG. 5A, lanes 2 and 3). In contrast, a substantial amount of IE72 protein was observed in cells infected with virus treated with either DMEM alone (lane 4) or in the presence of 680 nM $G_0$ RNA (FIG. 5A, lanes 1 and 4).

In the second set of experiments, cells were infected with HCMV pretreated with different concentrations of L19. Those cells that expressed IE72 were visualized by immunofluorescent microscopy with anti-IE72 antibody, mAb1203, and their numbers were counted (FIG. 5B). A significant reduction in the numbers of IE72-expressing cells was observed among cells infected with viruses pretreated with 680 nM L19 or 200 μg/ml anti-HCMV neutralizing antibodies nAb (FIG. 5B, (c) and (e)), while no reduction was observed in the presence of 680 nM $G_0$ [FIG. 5B, (f)]. The level of reduction in the numbers of IE72-expressing cells was dependent on the concentrations of L19, with an IC50 value of 35+7 nM (FIG. 5C).

These results suggest that L19 blocks a step prior to or during viral immediate-early gene expression, such as viral entry, uncoating, or transcription of IE72 mRNA. To distinguish among these possibilities, viral particles pretreated with different concentrations of L19 were incubated with human fibroblasts at 37° C. for 90 mins to allow viral entry.

Then, the cells were washed extensively and further trypsinized in order to remove the unbound viral particles and those extracellular viruses that still attached to the cells. Total DNA was isolated from these infected cells and the level of intracellular viral genomic DNA was determined by PCR detection of the sequence of viral immediate-early gene IE1/IE2. The level of human β-actin DNA was used as the internal control for the quantitation of HCMV DNA. A significant reduction in the level of intracellular HCMV DNA was observed in cells infected with virus treated with L19, indicating that the entry of the viral genome was blocked. As a control, no HCMV DNA was detected in cells infected with viruses either pretreated with 200 μg/ml nAb or 50 μg/ml heparin which blocked HCMV attachment. When viral infection was carried out at 4° C. to allow viral attachment but prevent penetration, intracellular HCMV DNA was barely detected (lane 9). These experiments strongly suggest that both the unbound viruses and those attaching to the cells were almost completely removed by the washing procedures and the HCMV DNA detected by PCR probably represented the viral genome that had entered the cells. Pretreatment of HCMV with 35 nM of L19 yielded a reduction of 55% in the level of viral DNA (FIG. 6).

If inhibition of viral entry is the only block by L19 to a single cycle of viral replication, reduction of the input viral DNA and of the viral yield and gene expression should be quantitatively similar. Our results (FIGS. 3–6) indicate that there is an excellent correlation among the level of reduction in the viral input DNA, the level of inhibition of IE72 gene expression, and viral production. For example, the treatment of HCMV with 35–40 nM of L19 yielded a reduction of 50–55% in the level of viral input DNA, the numbers of IE72-expressing cells, and the level of viral plaque formation and growth. Thus, L19 appeared primarily to block the viral entry step.

Figure 6:
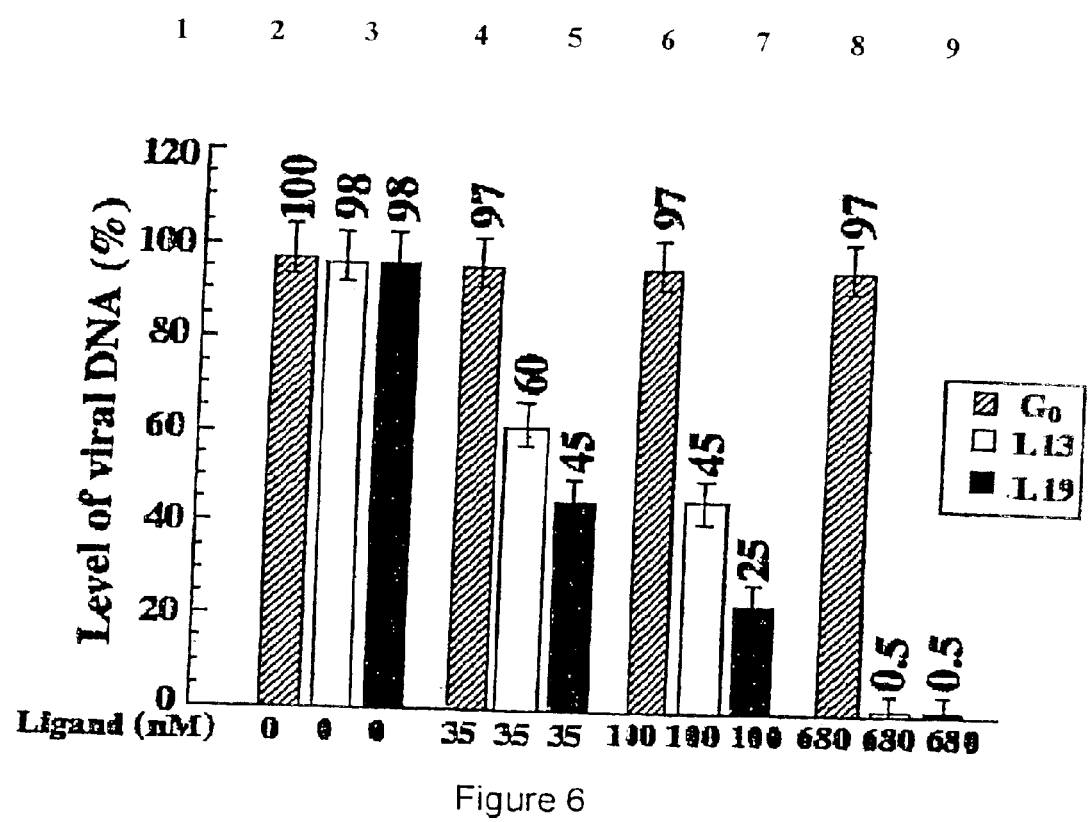

Similar experiments have also been carried out to determine which steps(s) of the viral lytic cycle is blocked by L13 (FIGS. 5C and 6B). For example, the treatment of HCMV with 100 nM of L13 yielded a reduction of about 50% in the level of viral input DNA (FIG. 6), the numbers of IE72-expressing cells (FIG. 5C), and the level of viral plaque formation and growth (FIGS. 3A and 3B). These results suggest that L13 also functions to block viral entry.

It is possible that L19 and L13 may block viral entry by interacting with a cellular surface receptor rather than a viral surface molecule. To distinguish between these possibilities, cells were preincubated with different concentrations of L19 or L13 (up to 3000 nM) and then washed before infected with HCMV. No reduction in the level of viral plaque formation or IE72 protein expression was observed. Moreover, these ligands did not exhibit significant cytotoxicity. Cells that were treated with 3000 nM L19 or L13 every other day for 30 days were indistinguishable from the untreated ones with respect to viability and plating efficiency at days 1, 2, 4, and 8 after seeding. These observations suggest that the observed antiviral effects by L19 and L13 are due to their high affinity binding to the viral particles but not interactions with the cells.

Identification of viral targets bound by L13 and L19. The protein assays of the infectious HCMV virions indicated that a stock of $1 \times 10^5$ PFU virus approximately contained 10 μg of protein. When the complexes formed between HCMV and L13 or L19 were treated with proteinase K to remove most of the viral surface glycoproteins, the majority of the bound ligands were found to be dissociated from the viral particles. This observation suggested that these ligands bind to viral proteins. To identify the viral targets to which L19 and L13 bind, the complexes formed between HCMV particles and radiolabeled L19 and L13 molecules were UV irradiated to allow crosslinking and then, separated on SDS-denaturing polyacrylamide gels. Those proteins that bound to L19 and L13 were expected to crosslink with the ligand and become radiolabeled. Two crosslinked products with apparent molecule masses of about 170 and 55 kDa were found in the experiments with L19 and were immunoprecipitated by a monoclonal antibody specifically against HCMV glycoprotein B (gB). gB is one of the most abundant viral glycoproteins and is required for HCMV entry. The full-length gB protein has an apparent molecular mass of about 170 kDa and is proteolytically processed into an amino terminal product of 115 kDa and a carboxyl terminal product of 55 kDa (gp55). Indeed, the crosslinked products comigrated with the gB products found in the HCMV particles (lane 8). Therefore, L19 appeared to bind to gB. Meanwhile, a protein product with an apparent molecule mass of about 90 kDa was found to crosslink with L13 and was immunoprecipitated by a monoclonal antibody specifically against HCMV glycoprotein H (gH). gH is also a viral abundant glycoprotein essential for HCMV entry and has an apparent molecular weight of 86 kDa (gp86). The crosslinked conjugates with L19 and L13 were not observed either in the absence of the UV irradiation or when the crosslinked mixture was digested with protease K before separated on SDS-polyacrylamide gels (lanes 2 and 10). Moreover, the products crosslinked with L19 were not immunoprecipitated with the anti-gH antibody while that crosslinked with L13 was not recognized by the anti-gB antibody. The specificity of the crosslinks was also investigated in competition experiments with homologous and heterologous competitors. For example, the formation of the crosslinked species with L19 was blocked in the presence of the non-radiolabeled L19 but not L13 or $G_0$. These results suggest a specific interaction between L19 and these two gB products. Similar results were also observed to suggest that L13 specifically interacts with gH.

Nucleic acid-based ligands isolated from randomized sequences have been shown in vitro to exhibit high affinity and specificity to a wide variety of low molecular weight targets and large complexes such as red blood cell membranes. More recently, this approach has also been used to select RNA aptamers to bind to intact infectious agents such as Rous sarcoma virus (RSV) and African trypanosome. Compared to monoclonal and polyclonal antibodies, nucleic acid-based ligands possess similar activity (high affinity and specificity) as well as other unique features. For example, the nature of the interactions (e.g. nucleic acid—protein interactions) between these ligands and their protein targets might be different from those (e.g. protein—protein interactions) used between antibodies and the same targets. Therefore, targets that are not considered immunogenic to antibodies may be tightly bound by RNA ligands. Using HCMV as a model system, we showed that ribonuclease-resistant RNA ligands were isolated from randomized sequences to bind HCMV particles and were very effective in blocking viral entry by interacting with different viral glycoproteins.

Binding affinity and specificity of the antiviral RNA ligands. Several criteria have to be satisfied in order to use these RNAs as antiviral neutralizing agents. For example, their binding affinity and substrate specificity should be high, and their activity should be stable. In our study, the selected ligands exhibited a high affinity to HCMV particles and were highly effective in inhibiting viral production.

Most of our ligands bound to the target tightly, and it only required 35–50 nM of L19 to interact with $1\times10^5$ pfu/ml viral particles and inhibit infection by 50% (FIGS. 3–6). The binding affinity of the ligands also appeared to correlate with their activity in inhibiting viral infection. For example, the G16 ligands exhibited higher affinity to HCMV and were more effective in blocking viral infection than the G10 and G0 ligands. Moreover, ligands with higher binding affinity can be further isolated by increasing the stringency for binding during the selection. Meanwhile, consistent with previous observations, the 2'-amino pyrimidine modification significantly increases the stability of the selected ligands. These 2'-amino-substituted RNA ligands were very stable in culture media that contained HCMV and bovine serum.

Our results from three different sets of experiments also suggest that the selected ligands are highly specific. First, L13 and L19 did not compete for binding to HCMV (FIG. 2B). The combination of both L13 and L19 exhibited higher activity to inhibit viral plaque formation than that with either ligand (FIG. 4). These results are consistent with our suggestion that L13 and L19 specifically recognize different viral proteins (i.e. gH and gB) required for infection. Second, L13 and L19 blocked viral growth in cells that were infected with two different strains of HCMV but not with the related HSV-1. These ligands in vitro exhibited 104 fold less binding affinity to HSV than to HCMV. HSV and HCMV share several homologous glycoproteins, three of which (gB, gH, and gL) have been shown to be required for viral infectivity and entry. Our observations suggest that these ligands interact with unique viral epitopes found in the gB and gH of HCMV but not of HSV. Finally, the selected ligands exhibited little cytotoxicity. When human foreskin fibroblasts were treated with 3000 nM of L19, a concentration four-time higher than that required to abolish the infection of $1\times10^5$ pfu/ml of HCMV, they are indistinguishable from the untreated ones with respect to viability and plating efficiency. Moreover, their protein expression profiles were the same and no morphological differences were detected.

Mechanism of the antiviral activity of the selected ligands. None of the sequences of the selected ligands has extensive homology to both strands of the HCMV DNA genomic sequence, suggesting that the selected ligands do not function as antisense agents. Inhibition of viral infection was observed when HCMV was either preincubated with the ligands before introduced to the cells or was co-introduced to the cells with the ligands (FIG. 3). Several lines of evidence suggest that L19 and L13 inhibit viral production and plaque formation by primarily blocking the entry of viral genome. The level of intracellular viral DNA, determined by PCR, probably reflects that of viral input genome during entry. Our data indicated that there is an excellent correlation among the level of reduction in the viral input DNA, the level of inhibition of IE72 gene expression, and viral production. These results strongly suggest that the inhibition of the entry of the viral genome into the cells is primarily responsible for all the observed antiviral effects by L19 and L13.

L19 and L13 crosslink predominately with two proteins of about 170 kDa and 55 kDa, and a single protein of approximate 90 kDa, respectively. These proteins were immunoprecipitated by anti-gB and anti-gH antibodies, suggesting that they are gB and gH. This is further supported by the fact that the size of these proteins are consistent with those of gB (170 and 55 kDa) and gH (86 kDa). Our observations that only these proteins but not other proteins were found predominately in the crosslink complexes also suggest that L19 and L13 primarily interact with gB and gH, respectively.

gB and gH are among the most abundant glycoproteins on the surface of HCMV. These two proteins are essential for viral entry and neutralizing antibodies that block viral infection have been isolated. L19 and L13 bind to novel neutralizing epitopes of gB and gH that are different from those identified by antibodies, given the fact that these ligands recognize their targets through RNA-protein interactions. This is further supported by the fact that binding of L19 to HCMV is not affected by the presence of 3 different anti-gB neutralizing antibodies.

Generation of ligands as a research tool and as a therapeutic agent. In vitro selection procedure has provided a powerful approach to isolate RNA ligands that bind to intact infectious agents. Isolation of RNA ligands that target several different strains of a single agent or multiple agents can be easily accomplished by combining these agents together in the selection. Using a filter with a maximum pore size of 50 nm in the selection procedure will further facilitate the selection, of RNA ligands with high affinity to almost any infectious agents. Crosslinking procedures with the selected ligands should facilitate rapid identification of the targets of the infectious agents required: for infectivity. Our results that the selected ligands bind to gB and gH further demonstrate the utility of the selection procedure to isolate ligands that recognize different abundant protein targets on the surface of an infectious agent.

HCMV, one of the largest human viruses, has the coding capacity for more than 220 open reading frames, 57 of which have been predicted to encode membrane proteins. To date, however, fewer than 10 virion envelope glycoproteins have been mapped to the viral genome and only four of them (gB, gH, gL, gO) have been implicated to be essential for viral entry. Further studies using the selected ligands may lead to identification of new viral surface proteins that are important for infectivity. Identification of new viral essential glycoproteins will further our understanding of HCMV infection and provide novel targets for drug development. The above data greatly facilitates the development of these ligands as tools to study the biology of viral infection and as therapeutic agents for antiviral applications.

Materials and Methods

Viruses, cells and antibodies. HCMV (AD169 and Towne strain) and human foreskin fibroblasts (HFFs) were obtained from American Tissue Culture Collection (ATCC) (Rockville, Md.) and Clonetics Inc. (San Diego, Calif.), respectively. The HFFs were maintained and propagated in Dulbecco's modified Eagle's medium (DMEM) supplemented with 10% fetal bovine serum. HSV-1 (F), a prototype of human herpes simplex virus 1, was a gift from Dr. Bernard Roizman of the University of Chicago. The anti-IE72 monoclonal antibody, mAb1203, and a mixture of anti-HCMV glycoprotein B (gB) neutralizing monoclonal antibodies (nAb), mnAb1204, 1206, and 1212, were obtained from Goodwin Cancer Research Institute (Plantation, Fla.). The monoclonal antibody against gH was purchased from Biodesign Inc (Kennebunk, Me.).

HFFs were infected with HCMV and the viral particles were purified by double tartrate glycerol ultracentrifugation procedures. The infectivity of the purified HCMV was evaluated by titering the particles in HFFs while the intactness of their structures was examined first by obtaining negative staining images with a conventional transmission electron microscope (UC-Berkeley Electron Microscopy Core Facility) and further confirmed by electron cryomicroscopy.

In vitro selection procedure. Double-stranded DNA templates were synthesized by PCR using oligonucleotide JH101 (SEQ ID NO:29) (5'-GCCGGATCCGGGCCTCATGAT-GAANNNNNNNNNNNNNNNNNNNNNNNNNNNNNNNNNNNNNNNNTTGACCGTTTATTCTTGTCTCC-3') as the template. JH101 contained a randomized sequence indicated as $(N)_{40}$ and underlined. The 5' and 3' PCR primers were oligodeoxynucleotides JH1031 (SEQ ID NO:30) (5'-CCGAAGCTTAATACGACTCACTATAGGGAGACAAGAATAAACGGTCAA-3') and JH1052 (5'-CCCTCATGTCGAA-3'), respectively. JH1031 also contained the promoter sequence for bacteriophage T7 RNA polymerase. Transcription reactions were carried out in 40 mM Tris.HCl, pH 7.9, 6 mM $MgCl_2$, 10 mM DTT, 2 mM spermidine, 0.5 mM each of ATP and GTP, and 1 mM each of 2' amino-UTP and 2' amino-CTP (Amersham Inc. Arlington Heights, Ill.) in the presence of $\gamma$-[$^{32}$P]-GTP and T7 RNA polymerase for 16 hrs at 37° C. The synthesized RNA ligands were further purified in denaturing 8% polyacrylamide gels and then denatured in buffer I (20 mM Tris, pH 7.5, 100 mM NaCl) at 90° C. for 3 mins. The RNA ligands were incubated at 37° C. with different amounts of HCMV in buffer III (20 mM Tris, pH 7.5, 100 mM NaCl, 2.5 mM $MgCl_2$) for 15 mins. The mixtures were then passed through a Millipore membrane of 50 nm pore size which had been pre-equilibrated with buffer III. After an extensive wash, the membranes were soaked under denaturing conditions in buffer IV (10 M Urea, 20 mM Tris pH 7.5, 5 mM EDTA) to allow the RNA ligands to be released from the bound complexes. RNA ligands were finally purified by phenol/chloroform extraction followed by ethanol precipitation and were used as templates for reverse transcription in the presence of 7.5 $\mu$M of primer JH1052 and avian myoblastosis virus (AMV) reverse transcriptase (Promega Inc. Madison, Wis.). The synthesized cDNA was subsequently amplified by PCR with oligodeoxynucleotide primers JH1031 and JH1052 and was used to generate RNA ligands for the next round of selection. PCR was carried out in a reaction mixture (100 $\mu$l) that contained 10 mM Tris.HCl, pH 8.3, 15 mM $MgCl_2$, 0.01% gelatin, 50 mM KCl, 0.2 mM dNTPs, 1 unit Taq DNA polymerase (Perkin-Elmer) and 100 pmol each of oligodeoxynucleotides JH1031 and JH1052.

Initially, 2 nmol of the pool of RNA ligands that contained the randomized sequence were mixed with $1\times10^9$ pfu of HCMV in a volume of 5 ml. In subsequent cycles of selection, 10 pmol of RNA ligands were used and mixed with HCMV in a volume of 500 $\mu$l. During the first four cycles of selection, viral particles of $5-10\times10^6$ pfu were used. During the selection cycles 5–8, 9–12 and 13–16, the amounts of HCMV used were reduced to $1\times10^5$, $5\times10^3$, and $5\times10^2$ pfu, respectively. The affinity of the RNA ligand population after every other cycle of selection was assayed to monitor the selection progress. After sixteen cycles of selection, cDNA that contained ligand sequences was cloned into pUC19 and sequence analysis was performed with Sequenase in the presence of [$^{35}$S]-ATP (Amersham Inc. Arlington Heights, Ill.).

In vitro assays for binding of selected RNA analogs to HCMV particles. Binding assays were carried out by mixing 5$\mu$l of different concentrations of HCMV to 45 $\mu$l of either binding buffer III (20 mM Tris, pH 7.5, 100 mM NaCl, 2.5 mM $MgCl_2$) or culture media DMEM which contained 10,000–100,000 cpm of RNA ligands (less than 100 fmol). The mixture was incubated at 37° C. for 15 mins and then passed over a 50 nm pore size filter, which was either pre-equilibrated in buffer III or culture medium DMEM. After extensive wash, the filter was dried and the radioactivity was quantitated with a STORM840 Phosphorimager. Each binding curve consisted of at least six points and each point represented the averages of values obtained from at least two independent experiments.

Viral infection and assays of the antiviral activity of the ligands. A well (of a six or 24 well dish) of cells (approximately $1-5\times10^5$ cells) were either mock infected or infected with HCMV at a MOI of 0.001–0.01 (for plaque assay) or 0.2–1 (for viral yield assays) in an inoculum of 200 $\mu$l (for 24 well plates) or 500 $\mu$l (for 6 well plates). The viruses were preincubated at 37° C. for 15 mins with DMEM alone or DMEM that contained different concentrations of L13, L17, L19, G0, or nAb, a mixture of anti-HCMV gB neutralizing antibodies. After a 2 hour exposure to the virus at 37° C., the cells were extensively washed to remove unbound viruses and then incubated with DMEM supplemented with 10% fetal bovine serum. The infected cells were incubated for a certain period time (as stated in the result section) for plaque assays or before being harvested for titration of viral yields. To determine the viral yields, viral stocks were prepared by sonicating the infected cell lysates, and their titers were determined by infecting $1\times10^5$ HFF cells in 24 well plates and counting the number of plaques 10–14 days postinfection.

Isolation of protein extracts, electrophoretic separation and staining of infected cellular polypeptides with antibodies. To prepare protein extracts, cells were harvested, washed, and lysed as described previously (Liu and Altman (1995) *Genes* & *Dev.* 9:471–480). The proteins were separated on 9% [vol/vol] SDS-polyacrylamide gels cross-linked with N,N"-methylenebisacylamide, transferred electrically to nitrocellulose membranes and stained with anti-mouse IgG conjugated with horseradish peroxidase and the mAb1203 antibody against HCMV IE72. To quantify the expression levels of viral IE72, the membranes were stained with a chemilluminescent substrate (Amersham Inc, Arlington Heights, Ill.) and subsequently scanned in a STORM840 phosphorimager (Molecular Dynamics, Sunnyvale, Calif.).

Assays of number of cells expressing IE72 and the intracellular level of viral DNA. Immunofluorescent staining of cells that expressed IE72 was used to determine the number of the infected cells as described previously (Navarro et al., (1993) *Virology* 197:143–158). In brief, $10^5$ cells grown on 10-mm round coverslips were infected with viruses that were pretreated with DMEM containing different concentrations of L19 or $G_0$. After a 1.5 hour incubation at 37° C., cells were extensively washed and then incubated with fresh media containing 10% fetal bovine serum. At 36 hours after infection, cells were fixed with acetone and methanol mixture (1:1, v/v) for 20 mins and washed three times in phosphate-buffered saline (PBS). The fixed cells were incubated with anti-IE72 monoclonal antibody, mAb1203 (diluted 1:500 in PBS), for 30 mins, and then rinsed three times in PBS, followed by a 30-min incubation with anti-mouse IgG-fluorescein isothiocyanate antibody (Vector Labs, Burlingame, Calif.) diluted 1:250 in PBS. The stained cell nuclei were visualized by fluorescence microscopy and their numbers were counted. At least 10 microscopic fields (40×), corresponding to at least 3,000 cells, were scored for specific nuclear staining and the average of the numbers of the staining cells was calculated.

Viral DNA was detected by PCR amplification of the viral immediate-early IE1/IE2 sequence. The 5' and 3' primers were CMV3 (SEQ ID NO:32) (5'-CCAAGCGGCCTCTGATAACCAAGCC-3') and CMV4 (SEQ ID NO:33) (5'-CAGCACCATCCTCCTCTTCCTCTGG-3'), respectively.

PCR cycles and other conditions were optimized to assure that the amplification was within the linear range. To obtain the PCR DNA template, $5\times10^5$ cells grown on six-well plates were infected with viruses that were pretreated with DMEM alone or DMEM that contained 200 µg/ml anti-HCMV gB neutralizing antibodies, 50 µg/ml heparin, or different concentrations of L19 and G0. After a 1.5 hour incubation at 37° C., the inoculum was removed and cells were washed three times with PBS. Then the cells were treated with 0.25% trypsin and harvested. The harvested cells were further treated with 200 µg/ml trypsin at 37° C. for 10 mins and washed with PBS. Under these conditions, most of HCMV surface glycoproteins were digested and were not detectable. The trypsin treatment and wash with PBS was repeated three times in order to completely remove the unbound viruses and those that still attached to the cells. The cell pellet was resuspended in the lysis buffer (50 mM Tris, pH 9.0, 1 mM EDTA, 100 mM NaCl) containing 500 µg/ml Proteinase K and 1.0% SDS and incubated at 55° C. for 2 hours. The digested mixture was extracted with phenol/chloroform three times and chloroform once followed by ethanol precipitation to generate the PCR DNA templates. The PCR reaction consisted of 20 cycles with denaturation at 94° C. for 1 min, followed by primer annealing at 47° C. for 1 min and extension at 72° C. for 1 min. The last cycle was again an extension at 72° C. for 10 min. Human β-actin sequence was used as the internal control. The 5' and 3' primers used to amplify the actin sequence were Actin5 (SEQ ID NO:34) (5'-TGACGGGGTCACCCACACTGTGCCCATCTA-3') and Actin3 (SEQ ID NO:35) (5'-CTAGAAGCATTGCGGTGGCAGATGGAGGG-3'), respectively (Stratagene Inc. La Jolla, Calif.). The amplified HCMV DNA (481 bp) and actin sequence (610 bp) were separated on either 1% agarose gels or 4% nondenaturing polyacrylamide gels.

To quantitate the level of viral DNA, PCR reactions were carried out in the presence of $\gamma$-$[^{32}P]$-dCTP. The radiolabeled DNA samples separated on either agarose or polyacrylamide gels were scanned with a STORM840 phosphorimager. A standard (dilution) curve was generated by amplifying different dilutions of the template DNA. The plot of counts for both HCMV and β-actin vs dilutions of DNA did not reach a plateau for the saturation curve under the conditions described above, indicating that quantitation of viral DNA could be accomplished. The fact that the ratio of viral DNA to β-actin remained constant with respect to each DNA dilution in the standard curve indicated the adequate accuracy and reproducibility of the assay. The PCR results were derived from three independent experiments.

UV crosslinking experiments. UV crosslinking between the uniformly $[^{32}P]$ labeled ligands and HCMV was carried out essentially as described by Guerrier-Takada et al (1989) *Science* 246:1578–1584. To prevent nonspecific binding of the ligands to HCMV, HCMV was mixed with the radiolabeled ligand in the presence of a 20 fold molar excess of tRNA$_{Tyr}$ molecules. Binding of L19 and L13 to HCMV was not affected in the presence of tRNA$_{Tyr}$ (FIG. 2B) and binding of tRNA$_{Tyr}$ to HCMV did not reduce the infectivity of HCMV particles. In the competition experiments with G0, L13, or L19, these nonradiolabeled ligand molecules were included in the mixture and were in 20 fold molar excess to the radiolabeled ligands. The radiolabeled RNA ligands (5–10 nM) as well as tRNA$_{Tyr}$ and nonradiolabeled ligand molecules were incubated with HCMV virion ($1\times10^4$ PFU) in binding buffer III (20 mM Tris, pH 7.5, 100 mM NaCl, 2.5 mM MgCl$_2$) for 15 mins at 37° C. Then, the reaction mixture was exposed to UV light (254 nm) for 5–15 mins and then digested with 40 µg/ml RNase A, 60 units/ml RNase T1, and 400 units/ml S1 nuclease for 30 mins. The crosslinked mixtures were either immunoprecipitated first with monoclonal antibodies against HCMV-gB or gH or directly denatured in the disruption buffer (0.05 M Tris, pH 7.0, 8.5% [vol/vol] sucrose, 5% [vol/vol] β-mercaptoethanol, 2% [vol/vol] sodium dodecyl sulphate). The immunoprecipitation was carried out as described previously (Meyer et al., 1990 *J. Gen Virol.* 71:2443–2450). The protein samples were boiled for 1 min, then subjected to electrophoretic separation in 7.5% [vol/vol] SDS-polyacrylamide denaturing gels, and finally analyzed by a STORM840 phosphorimager.

Example 2

Results

Figure 7:
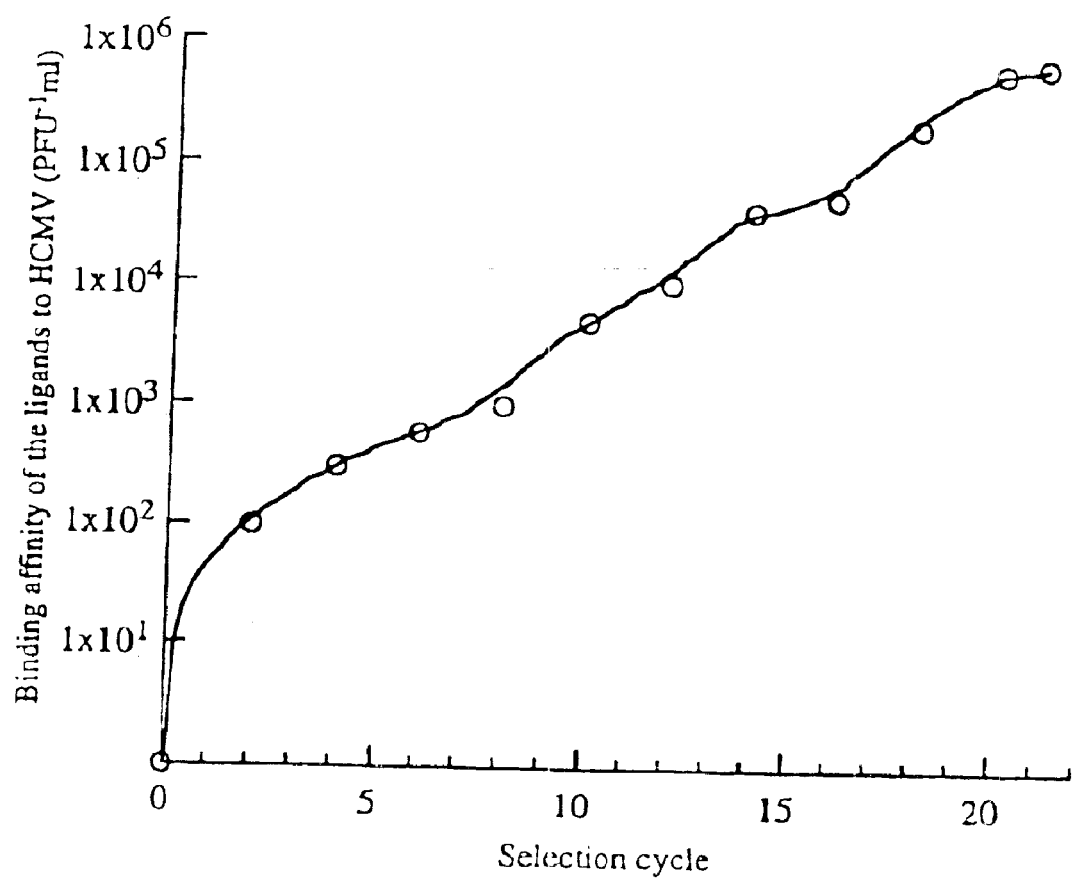
FIG. 7. Increased binding affinity of the populations of RNA ligands during selection from cycle 0 to cycle 21. The values of binding affinity were calculated by dividing the percentage of bound ligands with the concentration of HCMV used (PFU/ml). Each point represents the mean of duplicate measurements.

Isolation of RNA-based ligands that specifically bind to surface proteins of HCMV particles. The procedures for synthesis and selection were as essentially as described in Example 1, but in the final selection cycles (cycles 17–21), the filters were subjected to digestion by proteinase K. The process was repeated twenty-one times, and the binding affinity (measured as the value of binding percentage/viral concentration) of the ligand population after twenty-one cycles was higher than that of the initial randomized RNA (G$_0$) by a factor of more than $5\times10^5$ (FIG. 7).

The RNA analog molecules were allowed to bind to HCMV, and the mixtures passed through a 50 nm pore-size filter. Because HCMV is more than 200 nm in diameter, the bound ligands along with the viral particles were retained on the filter while those unbound passed through. During the first 16 cycles of selection, the washed filters were incubated in the presence of urea in order to release the bound ligands. Upon proteinase K digestion, only the ligands that bound to the surface proteins of HCMV particles were expected to be released while those that bound to the filters or the lipid bilayers of the HCMV envelope were retained. The cDNA molecules were synthesized and amplified by RT-PCR from the ligands that were released from the filters upon treatment of urea or proteinase K.

In vitro characterization of the selected ligands. Twenty-eight sequences coding for the ligands after twenty-one rounds of selection were cloned and characterized (Table 2) These ligands were divided into three sets based on their primary nucleotide sequences. Each sequence in sets VII and VIII either had the same sequence or extensive homology to other sequences of the same set. In contrast, the three sequences in set IX were unrelated to each other and to any other sets. The selected sequences were not found in the genomic sequence of HCMV, indicating that the selected sequences were neither derived from the viral genomic sequence or antisense to the HCMV sequences.

Figure 8:
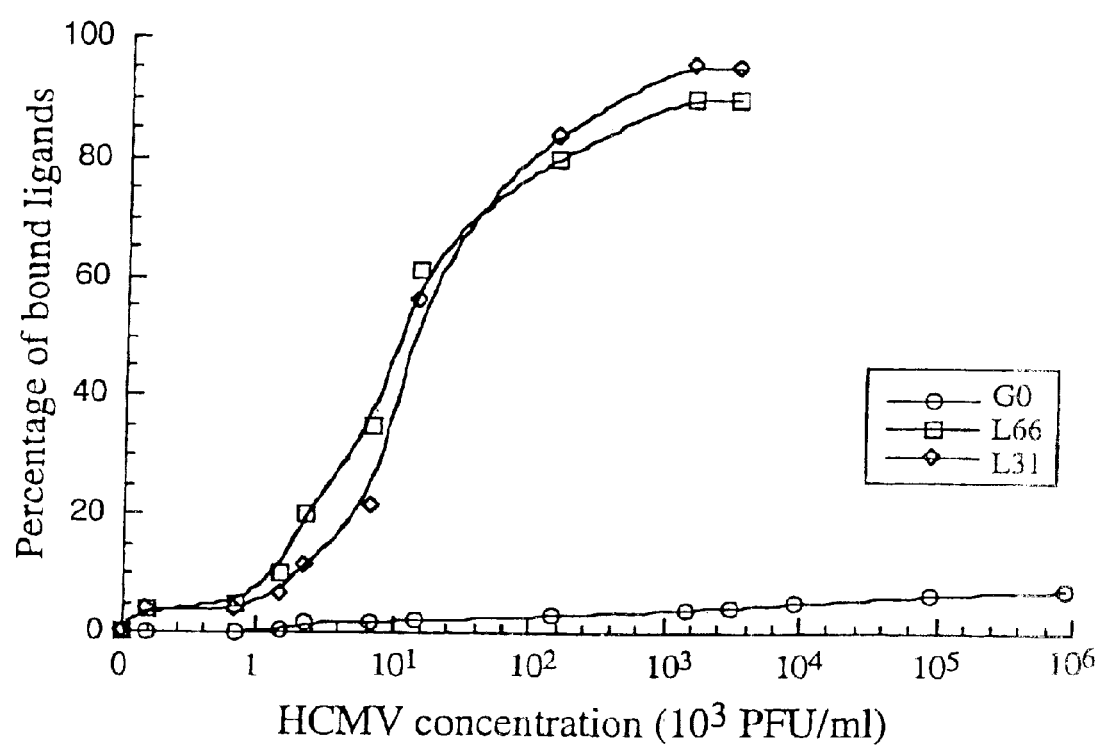
FIG. 8. Binding affinity of the selected ligands to HCMV. 0.2 nM of different selected ligands were allowed to bind to different concentrations of HCMV particles. The values for the percentage of binding represent the mean of triplicate experiments and are not significantly different when 0.1 nM–0.5 nM of ligands were used in the binding assays.

To analyze the relationship between the sequences of the selected ligands and their capabilities to bind HCMV, ligands L66 and L31 were assayed for their binding affinities to the viral particles. These molecules were chosen as representatives of the most abundant selected sequences (Table 2). A trace amount of radiolabeled ligands was incubated with different concentrations (PFU/ml) of HCMV in binding buffer C (20 mM Tris, pH 7.5, 100 mM NaCl, 2.5 mM MgCl$_2$), which was used in the selection. More than 50% of the ligands was bound in the presence of 10$^4$ PFU/ml HCMV (FIG. 8). In contrast, less than 10% of the G$_0$ molecules remained bound even in the presence of $1\times10^9$ PFU/ml HCMV. The binding affinities of both L31 and L66 were at least $5\times10^5$ higher than that of the initial randomized pool (FIG. 7, FIG. 8). L66 and L31 also exhibited similar binding affinities when binding assays were carried out in Dulbecco's modified Eagle media (DMEM) which resembled the physiological buffer conditions. RNase A digestion of the ligands before binding resulted in the loss of the binding capability of these molecules, indicating that the intact structure of the ligands is essential for HCMV binding.

Antiviral activity of the selected ligands. To determine whether the binding of selected ligands could interfere with the viral replication process and block infection, purified HCMV particles were first preincubated with different concentrations of ligands L31, L66, and G0 to allow for binding, and then used to infect human foreskin fibroblasts at a MOI of 0.02. After absorption, cells were washed with culture medium (DMEM) to remove residual virus. Then the cells were overlaid with 0.5% agarose and incubated at 37° C. and the number of viral plaques was counted at 10–14 days postinfection. A significant reduction of viral plaque formation was observed in cells infected with viruses that were pretreated with L66 but not with L31 and $G_0$ (FIG. 9A). The observed level of inhibition of viral plaque formation by L66 was concentration dependent. Results from triplicate experiments indicated that the concentration ($IC_{50}$) of L66 for 50% inhibition of plaque formation by $1 \times 10^5$ PFU/ml HCMV is 15±5 nM (FIG. 9A).

Figure 10:
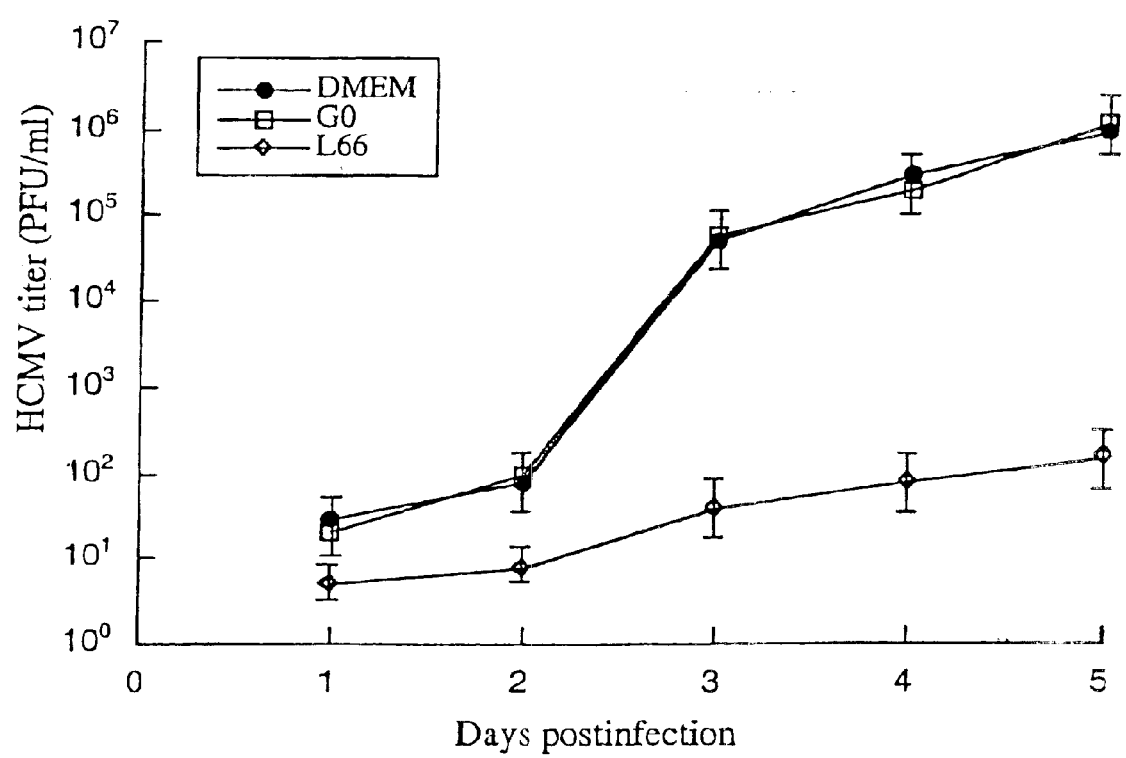
FIG. 10. Growth curve analysis of HCMV in human fibroblasts. $1\times10^5$ PFU/ml HCMV (AD169) was incubated in DMEM media alone (DMEM) or in the presence of 300 nM of $G_0$ ($G_0$) or L66 (L66) at 37° C. for 15 mins before being used to infect HFFs at a MOI of 2. Virus stocks were prepared from the infected cells at 1 day intervals through 5 days postinfection and the PFU count was determined by measurement of the viral titer on human fibroblasts. These values are the means from triplicate experiments. The standard deviation is indicated by the error bars.

To determine whether viral growth is inhibited by ligand binding, cells were first infected with viruses pretreated with L31, L66, and $G_0$, and then further incubated at 37° C. to allow HCMV to grow. After 36 and 72 hours postinfection, virus stocks were prepared from the infected cultures (cells and culture medium together) and the viral titers (PFU/ml) were determined in human fibroblasts. A significant reduction in viral yield was observed in experiments with L66, but not with L31 or $G_0$ (FIG. 9B). The inhibition of viral yield was also ligand dose-dependent, with an $IC_{50}$ for L66 equal to 18±4 nM, respectively. To further determine the inhibitory effects of the ligands on viral growth, cells were infected with HCMV (MOI=2) that was treated with 300 nM of $G_0$, L31, and L66, or without the ligands. Virus stocks were prepared from the infected cells at 1 day intervals through 5 days postinfection and the viral titers were determined in human fibroblasts (FIG. 10). After 4 days postinfection, a reduction of at least 5000 fold in viral yield was observed in cells that were infected with HCMV treated with L66, while no significant reduction was found in those treated with $G_0$ or L31 (FIG. 10). A reduction of viral plaque formation and viral growth was also observed when HCMV was first treated with L66 and then washed to remove most of the unbound ligands before being placed on cells.

Specific blockage of viral entry by L66. Three sets of experiments were carried out to study how L66 blocks viral growth and plaque formation. First, expression of the viral major immediate-early protein IE1, which is among the first proteins expressed after infection was determined. Human fibroblasts were infected with viruses that were pretreated with culture media (DMEM) alone, or in the presence of $G_0$, L66 or nAb, which is a mixture of anti-HCMV glycoprotein B (gB) neutralizing antibodies. The infected cells were harvested at 72 hours postinfection and proteins from the infected cells were separated electrophoretically on SDS-polyacrylamide gels, transferred to a nitrocellulose membrane, and finally stained with anti-IE1 antibody mAb1203s. The IE1 expression was barely detected in cells infected with HCMV pretreated with 300 nM of L66 or 200 μg/ml of anti-HCMV gB neutralizing antibodies nAb. In contrast, a substantial amount of IE1 was observed in cells infected with virus treated with either DMEM alone or with 300 nM of $G_0$ RNA.

In the second set of experiments, cells were infected with HCMV pretreated with different concentrations of L66. Those cells that expressed IE1 were visualized by immunofluorescent microscopy with mAb1203s and their numbers were counted. A significant reduction in the numbers of IE1-expressing cells was observed among cells infected with viruses pretreated with 300 nM L66 or 200 μg/ml anti-HCMV neutralizing antibodies nAb, while no reduction was observed in the presence of 300 nM $G_0$. The level of reduction in the numbers of IE1-expressing cells was dependent on the concentration of L66, with an $IC_{50}$ value of 15±7 nM (Table 3). These results suggest that L66 blocks a step prior to or during viral immediate-early gene expression, such as viral entry, uncoating, or transcription of IE1 mRNA.

TABLE 3

| Level of Inhibition | DMEM | Go 300 nM | L66 20 nM | L66 300 nM |
| --- | --- | --- | --- | --- |
| Viral DNA level (PCR) | 0% | 1% | 45 ± 4% | 98 ± 6% |
| IE1 protein | 0% | 0% | 42 ± 5% | 97 ± 8% |
| IE1-expressing cells | 0% | 0% | 45 ± 6% | 99 ± 8% |
| Plaque numbers | 0% | 2% | 40 ± 5% | 98 ± 10% |
| Viral growth | 0% | 1% | 45 ± 6% | 97 ± %6 |

To distinguish among these possibilities, the third set of experiments was carried out to determine whether L66 blocks viral entry. Viral particles pretreated with different concentrations of the ligand were incubated with human fibroblasts at 37° C. for 90 mins to allow viral entry. The cells were then washed extensively and further trypsinized in order to remove the unbound viral particles and those extracellular viruses that still attached to the cells. Total DNA was isolated from these infected cells and the level of intracellular viral genomic DNA was determined by PCR detection of the IE1 DNA sequence. The level of human β-actin DNA was used as the internal control for the quantitation of HCMV DNA. A significant reduction in the level of intracellular HCMV DNA was observed in cells infected with virus treated with L66 but not with $G_0$ (Table 3), suggesting that the entry of the viral genome was blocked. As a control, no HCMV DNA was detected in cells infected with viruses either pretreated with 200 μg/ml nAb or 50 μg/ml heparin which blocked HCMV attachment. When viral infection was carried out at 4° C. to allow viral attachment but prevent penetration, intracellular HCMV DNA was barely detected. These experiments strongly suggest that both the unbound viruses and those attaching to the cells were almost completely removed by the washing procedures, and the HCMV DNA detected by. PCR probably represented the viral genome that had entered the cells. Pretreatment of HCMV with 20 nM of L66 yielded a reduction of 45±4% in the level of viral DNA (Table 3).

If inhibition of viral entry is the only block by L66 in a single cycle of viral replication, reduction in the levels of the input viral DNA, the viral yield, and gene expression should be quantitatively similar. Our results indicate that there is an excellent correlation among the level of reduction in the viral input DNA, the level of inhibition of IE1 expression, and viral production. For example, the treatment of HCMV with 15–20 nM of L66 resulted in a reduction of 45–50% in the level of viral input DNA, the numbers of IE1-expressing cells, and the level of viral plaque formation and growth. Thus, L66 appears primarily to block the viral entry step.

The binding and antiviral activity of L66 appeared to be specific for HCMV. In vitro binding affinities of L66 for HCMV strain AD169 were similar to those for two other HCMV strains (Towne and Toledo), but were at least $1\times10^5$ fold higher than those for murine CMV (MCMV) Smith strain and herpes simplex virus 1 (HSV-1) strain F. L66 also inhibited plaque formation and growth of HCMV Towne and Toledo strains with a similar level of activity as for the AD169 strain. In contrast, no inhibition was observed when L66 was used with MCMV and HSV-1. These results indicate that the ligand specifically interacts with molecules that are commonly found in different HCMV strains but not in MCMV and HSV-1.

It is possible that L66 may block viral entry by interacting with a cellular surface receptor rather than a viral surface molecule. To distinguish between these possibilities, cells were preincubated with different concentrations of L66 (up to 1000 nM) and then washed before being infected with HCMV. No reduction in the level of viral plaque formation or IE1 expression was observed. Moreover, the ligand did not exhibit significant cytotoxicity. Cells that were treated with 1000 nM of L66 every other day for 30 days were indistinguishable from the untreated ones with respect to viability and plating efficiency at days 1, 3, 6, and 9 after seeding. These observations suggest that the observed antiviral effects by L66 are due to their high affinity binding to the viral particles and not their interactions with the cells.

Identification of viral targets bound by L66. As expected from our selection procedure, most of the bound ligands were found to be dissociated from the viral particles when the complexes formed between HCMV and L66 were treated with proteinase K to remove most of the viral surface glycoproteins. To identify the viral targets to which L66 binds, the complexes formed between HCMV and radiolabeled L66 were UV irradiated to allow for crosslinking and separated on SDS-polyacrylamide gels. Those proteins that bound to L66 were expected to crosslink with the ligand and become radiolabeled. Two major crosslinked products with apparent molecule masses of about 170 and 55 kDa were found in the experiments with L66 and were immunoprecipitated by a monoclonal antibody specifically against HCMV glycoprotein B (gB). The gB is one of the most abundant viral glycoproteins and is required for HCMV entry. The full-length gB protein has an apparent molecular mass of about 170 kDa and is proteolytically processed into an amino terminal product of 115 kDa and a carboxyl terminal product of 55 kDa (gp55). Indeed, the crosslinked products comigrated with the gB products found in infected cells and viral particles. Therefore, L66 appeared to bind to gB. The crosslinked conjugates associated with L66 were not observed either in the absence of the UV irradiation or when the crosslinked mixture was digested with proteinase K before being separated on SDS-polyacrylamide gels. The specificity of the crosslinks was also investigated in competition experiments with homologous and heterologous competitors. The formation of the crosslinked species with L66 was blocked in the presence of non-radiolabeled L66, but not $G_0$ or L31. These results suggest a specific interaction between L66 and these two gB products. Moreover, the formation of the crosslinked complexes was not blocked in the presence of a mixture of neutralizing antibodies against HCMV gB. These results suggest that L66 interacts with a region (epitope) of gB different from those recognized by the antibodies.

Mechanism of the antiviral activity of the selected ligands. As in Example 1, none of the sequences of the selected ligands (Table 2) has extensive homology to either strand of the HCMV DNA genomic sequence, suggesting that the selected ligands do not function as antisense agents. Inhibition of viral infection was observed when HCMV was either preincubated with L66 before being introduced to the cells or co-introduced to the cells with the ligand. Several lines of evidence suggest that L66 inhibits viral production and plaque formation by primarily blocking entry of the viral genome. The level of intracellular viral DNA, determined by PCR, probably reflects that of the input viral genome during entry. Our data indicate that there is an excellent correlation among the level of reduction in the viral input DNA, the level of inhibition of IE1 gene expression, and viral production. These results strongly suggest that the inhibition of the entry of viral genome into the cells is primarily responsible for all the observed antiviral effects by L66.

L66 crosslinks predominately with two proteins of about 170 kDa and 55 kDa. These proteins were immunoprecipitated by anti-gB antibodies, suggesting that they are gB proteins. This is further supported by the fact that the sizes of these proteins are consistent with those of gB (170 and 55 kDa). These proteins were not immunoprecipitated with either anti-gH or anti-gO antibodies, suggesting that L66 does not directly bind to gH or gO, both of which are essential for viral infectivity. Our observations that only these proteins but not other proteins were found predominately in the crosslink complexes also suggest that L66 primarily interacts with gB.

Our results demonstrate that the selected ligands are highly specific. L66, which was selected to bind to HCMV AD169 strain, blocked viral growth in cells that were infected with AD169 and two other strains of HCMV (Towne and Toledo) but not with the related MCMV and HSV-1. This ligand exhibited a $1\times10^5$ fold less binding affinity to MCMV and HSV than to HCMV in vitro. L66 appeared to interact with HCMV gB. The formation of crosslinked complexes between L66 and gB proteins was only blocked in the presence of L66 but not $G_0$ and L31. HSV, MCMV, and HCMV share several homologous glycoproteins, three of which (gB, gH, and gL) have been shown to be required for viral infectivity and entry. These ligands interact with unique viral epitopes found in the gB of HCMV but not of MCMV or HSV. Finally, the selected ligands exhibited little cytotoxicity. When human foreskin fibroblasts were treated with 1000 nM of L66, a concentration three times higher than that required to abolish the infection of $1\times10^5$ pfu/ml of HCMV, they were indistinguishable from the untreated ones with respect to viability and plating efficiency. Moreover, their protein expression profiles were the same and no morphological differences were detected (data not shown).

Modification of selection procedures for isolation of more effective ligands. In vitro selection procedure has provided a powerful approach for isolation of RNA ligands that bind to intact infectious agents. In this study, a filter with a maximum pore size of 50 nm was used in the selection procedure for isolation of RNA ligands with high affinity for HCMV. The inclusion of proteinase K digestion in the selection procedure will further enrich for ligands that specifically interact with the surface proteins of HCMV. Moreover, increasing selection stringency with a decreasing amount of HCMV particles will lead to the isolation of ligands that exhibit higher affinity. The majority of the ligands isolated in this study interact with specific HCMV surface proteins. Only 15–20 nM of L66 was required to interact with $1\times10^5$ pfu/ml viral particles and inhibit infection by 50% whereas 40–100 nM of L13 or L19 was needed to achieve the same effect. These results further demonstrate the feasibility of modifying the selection procedure for isolation of ligands that achieve optimal binding affinity and specificity for inhibition of HCMV infection.

Materials and Methods

Viruses, cells and antibodies. HCMV (AD169 and Towne strain) and murine CMV (MCMV) (Smith stain) were obtained from American Tissue Culture Collection (ATCC) (Rockville, Md.). The HCMV Toledo strain and HSV-1 F strain were gifts. Human foreskin fibroblasts (HFFs) were purchased from Clonetics (San Diego, Calif.) and maintained and propagated in Dulbecco's modified Eagle's medium (DMEM) supplemented with 10% fetal bovine serum. NIH 3T3 cells were obtained from ATCC and MCMV was propagated in NIH 3T3 cells. The anti-IE1 monoclonal antibody mAb1203s, anti-HCMV glycoprotein B (gB) antibody mAb 1201, and a mixture of anti-HCMV gB neutralizing monoclonal antibodies (nAb) (mAb1204, 1206, and 1212) were obtained from Goodwin Cancer Research Institute (Plantation, Fla.). Antibodies against HCMV gH (144b) and gO (anti-gO) were a gift. HFFs were infected with HCMV and the viral particles were purified by double tartrate glycerol ultracentrifugation procedures. The infectivity of the purified HCMV was evaluated by titering the particles in human fibroblasts and the intactness of their structures was examined first by obtaining negative staining images with a conventional transmission electron microscope and further confirmed by electron cryomicroscopy. Only those HCMV preparations that exhibited the highest titer (>$5\times10^8$ PFU/ml) and most intact particles were used for the selection.

In vitro selection procedure. DNA templates were synthesized by PCR using oligonucleotide FL111 (SEQ ID NO:42) (5'-GCCGGATCCGGGCCTCCTCATC-GAANNNNNNNNNNNNNNNNNNNNNNNNNNNNNN NNNNNNNNNNNNTTGACCGTTTATTCTTGTCTCC-3') as the template. FL 111 contained a randomized sequence indicated as (N)40 and underlined. Oligodeoxyribonucleotides FL5 (SEQ ID NO:43) (5'-CCGAAGCTTAATACGACTCACTATAGGGAGA AGAATAAACGGTCAA-3') and FL3 (SEQ ID NO:44) (5'-CCCTCATGTCGAA-3') were the 5' and 3' PCR primers, respectively. Transcription reactions were carried out in 40 mM Tris.HCl, pH 7.9, 6 mM $MgCl_2$, 10 mM DTT, 2 mM spermidine, 0.5 mM each of ATP and GTP, and 1 mM each of 2' amino-UTP and 2' amino-CTP (Amersham Inc. Arlington Heights, Ill.) in the presence of α-[$^{32}$P]-GTP and T7 RNA polymerase for 16 hrs at 37° C. The synthesized RNA ligands were further purified in polyacrylamide gels and then denatured in buffer A (20 mM Tris, pH 7.5, 100 mM NaCl) at 90° C. for 3 mins. The RNA ligands were incubated at 37° C. with different amounts of HCMV in buffer C (20mM Tris, pH 7.5, 100 mM NaCl, 2.5 mM $MgCl_2$) for 15 mins. The mixtures were then passed through a Millipore membrane of 50 nm pore size that had been pre-equilibrated with buffer C. After an extensive wash, the membranes were either soaked in buffer D (10 M Urea, 20 mM Tris pH 7.5, 5 mM EDTA) to allow the RNA ligands to be released from the bound complexes during the first 16 selection cycles, or incubated in buffer C in the presence of 100 μg/ml proteinase K for 30 mins during cycles 17–21. RNA ligands were finally purified by phenol/chloroform extraction followed by ethanol precipitation and were used as templates for reverse transcription with primer FL3 and AMV reverse transcriptase.

The synthesized cDNA was subsequently amplified by PCR with primers FL5 and FL3 was used to generate RNA ligands for the next round of selection. PCR was carried out in a reaction mixture (100 μl) that contained 10 mM Tris.HCl, pH 8.3, 15 mM $MgCl_2$, 0.01% gelatin, 50 mM KCl, 0.2 mM dNTPs, 1 unit Taq DNA polymerase (Perkin-Elmer) and 100 pmol each of oligodeoxynucleotides FL5 and FL3. Initially, 2 nmol of the pool of RNA ligands that contained the randomized sequence were mixed with $1\times10^9$ pfu of HCMV in a volume of 5 ml. In subsequent cycles of selection, 10 pmol of RNA ligands were used and mixed with HCMV in a volume of 500 μl. During the first four cycles of selection, viral particles of 5–$10\times10^6$ pfu were used. During the selection cycles 5–8, 9–12, 13–16, and 17–21, the amounts of HCMV used were reduced to $1\times10^5$, $5\times10^3$, $5\times10^2$, and 5×10' pfu, respectively. The affinity of the RNA ligand population after every other cycle of selection was assayed to monitor the selection progress. After twenty-one cycles of selection, cDNA that contained ligand sequences was cloned into pUC19 and sequence analysis was performed with Sequenase in the presence of α-[$^{35}$S]-ATP (Amersham Inc. Arlington Heights, Ill.).

Viral infection and assays of the antiviral activity of the ligands. Cells were either mock infected or infected with HCMV at a MOI of 0.02 (for plaque assay) or 0.5 (for viral yield assays). The viruses were preincubated at 37° C. for 15 mins with DMEM alone, or DMEM that contained different concentrations of L66, L31, $G_0$, or nAb, a mixture of anti-HCMV gB neutralizing antibodies (mAbs 1204, 1206, and 1212). After a 2 hour exposure to the virus at 37° C., the cells were extensively washed to remove unbound viruses and then incubated with DMEM supplemented with 10% fetal bovine serum. The infected cells were incubated for a period of time (as stated in the Result section) for plaque assays or before being harvested for titration of viral yields. To determine the viral yields, viral stocks were prepared by sonicating the infected cell lysates, and their titers were determined by infecting HFF cells and counting the number of plaques 10–14 days postinfection.

Binding assays of RNA ligands to HCMV particles and UV crosslinking experiments. Binding assays were carried out by mixing 5 μl of different concentrations of HCMV to 45 μl of either binding buffer C (20 mM Tris, pH 7.5, 100 mM NaCl, 2.5 mM $MgCl_2$) or culture media DMEM which contained about 20,000 cpm of RNA ligands (less than 50 fmol). The mixture was incubated at 37° C. for 15 mins and then passed over a 50 nm pore size filter, which was either pre-equilibrated in buffer C or culture medium DMEM. After an extensive wash, the filter was dried and the radioactivity was quantitated with a STORM840 Phosphorimager. Each binding curve consisted of at least six points and each point represented the averages of values obtained from at least two independent experiments.

UV crosslinking between the uniformly [$^{32}$P] labeled ligands and HCMV was carried out as described above. In order to prevent nonspecific binding of the ligands to HCMV, the virus was mixed with the radiolabeled ligand in the presence of a 20 fold molar excess of $tRNA^{Tyr}$ molecules. Binding of L66 to HCMV was not affected in the presence of $tRNA^{Tyr}$ and binding of $tRNA^{Tyr}$ to HCMV did not reduce the infectivity of HCMV particles. In the competition experiments with $G_0$ and L66, these nonradiolabeled ligand molecules were included in the mixture and were in 20 fold molar excess to the radiolabeled L66. The radiolabeled L66 (5–10 nM) as well as $tRNA^{Tyr}$ and nonradiolabeled ligand molecules were incubated with HCMV ($1\times10^4$ PFU) in binding buffer C (20 mM Tris, pH 7.5, 100 mM NaCl, 2.5 mM $MgCl_2$) for 15 mins at 37° C. Then, the reaction mixture was exposed to UV light (254 nm) for 5–15 mins and digested with 40 μg/ml RNase A, 60 units/ml RNase T1, and 400 units/ml S1 nuclease for 30 mins. The crosslinked mixtures were either immunoprecipitated first with monoclonal antibodies against HCMV-gB or directly denatured in the disruption buffer (0.05 M Tris, pH 7.0, 8.5% [vol/vol] sucrose, 5% [vol/vol] β-mercaptoethanol, 2% [vol/vol] sodium dodecyl sulphate). The immunoprecipitation was carried out as described previously. The protein samples were boiled for 1 min, then subjected to electrophoretic separation in 7.5% SDS-polyacrylamide gels, and finally analyzed by a STORM840 phosphorimager.

Analyses of HCMV IE1 expression. The infected cells were harvested, washed, and lysed as described previously. The proteins were separated on 9% SDS-polyacrylamide gels, transferred electrically to nitrocellulose membranes. To quantify the IE1 expression, the membranes were reacted with mAb1203s antibody against HCMV IE1, stained with a chemiluminescent substrate (Amersham Inc, Arlington Heights, Ill.), and subsequently scanned in a STORM840 phosphorimager (Molecular Dynamics, Sunnyvale, Calif.). Immunofluorescent staining of cells that expressed IE1 was used to determine the number of the infected cells as described previously. In brief, human foreskin fibroblasts grown on 10-mm round coverslips were infected with viruses that were pretreated with DMEM containing different concentrations of L66 or $G_0$. After a 1 hour incubation at 37° C., cells were extensively washed and then incubated with fresh media containing 10% fetal bovine serum. At 36 hours after infection, cells were fixed with acetone and methanol mixture (1:1, v/v) for 20 mins and washed three times in phosphate-buffered saline (PBS). The fixed cells were reacted with anti-IE1 monoclonal antibody mAb1203s, stained with anti-mouse IgG-fluorescein isothiocyanate antibody (Vector Labs, Burlingame, Calif.), visualized by fluorescence microscopy, and their numbers were counted. At least 10 microscopic fields (40x), corresponding to at least 3,500 cells, were scored for specific nuclear staining and the average of the numbers of the staining cells was calculated.

Quantitation of the intracellular level of viral DNA. Viral DNA was detected by PCR amplification of the viral IE1/IE2 sequence. The 5' and 3' primers were (SEQ ID NO:45) IE3 (5'-CCAAGCGGCCTCTGATAACCAAGCC-3') and (SEQ ID NO:46) IE4 (5'-CAGCACCATCCTCCTCTTCCTCTGG-3'), respectively (Demmler et al., 1988). PCR cycles and other conditions were optimized to assure that the amplification was within the linear range. To obtain the PCR DNA template, cells were infected with viruses that were pretreated with DMEM alone or DMEM that contained 200 μg/ml anti-HCMV gB neutralizing antibodies, 50 μg/ml heparin, or different concentrations of L66 and $G_0$. After a 1.5 hour incubation at 37° C., the inoculum was removed and cells were washed three times with PBS. Then the cells were treated with 0.25% trypsin and harvested. The harvested cells were further treated with 200 μg/ml trypsin at 37° C. for 10 mins and washed with PBS. The trypsin treatment and wash with PBS was repeated three times in order to completely remove the unbound viruses and those that still attached to the cells. The cell pellet was resuspended in the lysis buffer (50 mM Tris, pH 9.0, 1 mM EDTA, 100 mM NaCl) containing 500 μg/ml proteinase K and 1.0% SDS and incubated at 55° C. for 2 hours. The digested mixture was extracted with phenol/chloroform followed by ethanol precipitation to generate the PCR DNA templates. The PCR reaction consisted of 20 cycles with denaturation at 94° C. for 1 min, followed by primer annealing at 47° C. for 1 min and extension at 72° C. for 1 min. The last cycle was again an extension at 72° C. for 10 min. Human β-actin sequence was used as the internal control. The 5' and 3' primers used to amplify the actin sequence were (SEQ ID NO:47) Actin5 (5'-TGACGGGGTCACCCACACTGTGCCCATCTA-3') and (SEQ ID NO:48) Actin3 (5'-CTAGAAGCATTGCGGTGGCAGATGGAGGG-3'), respectively. PCR reactions were carried out in the presence of α-$[^{32}P]$-dCTP. The radiolabeled DNA samples containing the amplified HCMV DNA (481 bp) and actin sequence (610 bp) were separated on 4% nondenaturing polyacrylamide gels and scanned with a STORM840 phosphorimager. A standard (dilution) curve was generated by amplifying different dilutions of the template DNA. The plot of counts for both HCMV and β-actin vs. dilutions of DNA did not reach a plateau for the saturation curve (data not shown) under the conditions described above, indicating that quantitation of viral DNA could be accomplished. The fact that the ratio of viral DNA to β-actin remained constant with respect to each DNA dilution in the standard curve indicated the adequate accuracy and reproducibility of the assay. The PCR results were derived from three independent experiments.

What is claimed is:

1. A polynucleotide ligand composition comprising the sequence set forth in SEQ ID NO:12.

2. The polynucleotide ligand composition of claim 1, wherein said sequence comprises 2-amino pyrimidine nucleotides.

3. The polynucleotide ligand composition of claim 1, further comprising a pharmaceutically acceptable carrier.

4. The polynucleotide ligand composition of claim 3, wherein said polynucleotide ligand composition comprises two or more polynucleotides comprising distinct sequences.

5. A method of treating human cytomegalovirus infection, the method comprising:

administering an RNAse resistant RNA polynucleotide ligand composition at a dose sufficient to decrease said cytomegalovirus infection, wherein said polynucleotide composition comprises the sequence set forth in SEQ ID NO:12.

6. The method of claim 5, wherein said sequence blocks viral entry into a cell.

7. The method of claim 5, wherein said sequence comprises 2-amino pyrimidine nucleotides.

8. The method of claim 5, wherein said polynucleotide ligand composition comprises two or more polynucleotides comprising distinct sequences.

* * * * *

SEQUENCE LISTING

```
<160> NUMBER OF SEQ ID NOS: 52

<210> SEQ ID NO 1
<211> LENGTH: 40
<212> TYPE: DNA
<213> ORGANISM: Artificial Sequence
<220> FEATURE:
<223> OTHER INFORMATION: randomized sequence

<400> SEQUENCE: 1
ttacggtcac cttacccctg ggtgtgctct tcccggtggg                    40

<210> SEQ ID NO 2
<211> LENGTH: 40
<212> TYPE: DNA
<213> ORGANISM: Artificial Sequence
<220> FEATURE:
<223> OTHER INFORMATION: randomized sequence
```

-continued

```
<400> SEQUENCE: 2
ttacggtcac cttacccctg ggtgtgctct tcccggtggg                    40

<210> SEQ ID NO 3
<211> LENGTH: 40
<212> TYPE: DNA
<213> ORGANISM: Artificial Sequence
<220> FEATURE:
<223> OTHER INFORMATION: randomized sequence

<400> SEQUENCE: 3
tcacagtcac cttacccctg ggtgtgctct tcccggtggg                    40

<210> SEQ ID NO 4
<211> LENGTH: 40
<212> TYPE: DNA
<213> ORGANISM: Artificial Sequence
<220> FEATURE:
<223> OTHER INFORMATION: randomized sequence

<400> SEQUENCE: 4
tcacagtcac cttacccctg ggtgtgctct tcccggtggg                    40

<210> SEQ ID NO 5
<211> LENGTH: 40
<212> TYPE: DNA
<213> ORGANISM: Artificial Sequence
<220> FEATURE:
<223> OTHER INFORMATION: randomized sequence

<400> SEQUENCE: 5
ttacggtcac cttacccctg ggtgtgctct tcccggtggg                    40

<210> SEQ ID NO 6
<211> LENGTH: 40
<212> TYPE: DNA
<213> ORGANISM: Artificial Sequence
<220> FEATURE:
<223> OTHER INFORMATION: randomized sequence

<400> SEQUENCE: 6
tcacagtcac cttacccctg ggtgtgctct tcccggtggg                    40

<210> SEQ ID NO 7
<211> LENGTH: 40
<212> TYPE: DNA
<213> ORGANISM: Artificial Sequence
<220> FEATURE:
<223> OTHER INFORMATION: randomized sequence

<400> SEQUENCE: 7
gcgaattaac acatcgggcc catcgtccga ggtgcgtggg                    40

<210> SEQ ID NO 8
<211> LENGTH: 40
<212> TYPE: DNA
<213> ORGANISM: Artificial Sequence
<220> FEATURE:
<223> OTHER INFORMATION: randomized sequence

<400> SEQUENCE: 8
gcgaattaac acatcgggcc catcgtccga ggtgcgtggg                    40

<210> SEQ ID NO 9
<211> LENGTH: 40
```

```
<212> TYPE: DNA
<213> ORGANISM: Artificial Sequence
<220> FEATURE:
<223> OTHER INFORMATION: randomized sequence

<400> SEQUENCE: 9
gcgaattaac acatcgggcc catcgtccga ggtgcgtggg                    40

<210> SEQ ID NO 10
<211> LENGTH: 40
<212> TYPE: DNA
<213> ORGANISM: Artificial Sequence
<220> FEATURE:
<223> OTHER INFORMATION: randomized sequence

<400> SEQUENCE: 10
catctctcct caccataacct ccacttcctg ggctcgtggg                   40

<210> SEQ ID NO 11
<211> LENGTH: 40
<212> TYPE: DNA
<213> ORGANISM: Artificial Sequence
<220> FEATURE:
<223> OTHER INFORMATION: randomized sequence

<400> SEQUENCE: 11
catctctcct caccataacct ccacttcctg ggctcgtggg                   40

<210> SEQ ID NO 12
<211> LENGTH: 40
<212> TYPE: DNA
<213> ORGANISM: Artificial Sequence
<220> FEATURE:
<223> OTHER INFORMATION: randomized sequence

<400> SEQUENCE: 12
ctcgagccac cccataaccc tcaatactcc agggattggg                    40

<210> SEQ ID NO 13
<211> LENGTH: 40
<212> TYPE: DNA
<213> ORGANISM: Artificial Sequence
<220> FEATURE:
<223> OTHER INFORMATION: randomized sequence

<400> SEQUENCE: 13
ctcgagccac cccataaccc tcaatactcc agggattggg                    40

<210> SEQ ID NO 14
<211> LENGTH: 40
<212> TYPE: DNA
<213> ORGANISM: Artificial Sequence
<220> FEATURE:
<223> OTHER INFORMATION: randomized sequence

<400> SEQUENCE: 14
catcacttga ccctactcta cctgggctgg actgggtggg                    40

<210> SEQ ID NO 15
<211> LENGTH: 40
<212> TYPE: DNA
<213> ORGANISM: Artificial Sequence
<220> FEATURE:
<223> OTHER INFORMATION: randomized sequence

<400> SEQUENCE: 15
```

```
ctatttccca cccatatccc cttgggccct tgggtgtggg                    40

<210> SEQ ID NO 16
<211> LENGTH: 37
<212> TYPE: DNA
<213> ORGANISM: Artificial Sequence
<220> FEATURE:
<223> OTHER INFORMATION: randomized sequence

<400> SEQUENCE: 16
ctatatccac ccatatcccc ttccccttgc gtgtggg                       37

<210> SEQ ID NO 17
<211> LENGTH: 40
<212> TYPE: DNA
<213> ORGANISM: Artificial Sequence
<220> FEATURE:
<223> OTHER INFORMATION: randomized sequence

<400> SEQUENCE: 17
gcacgactct cactcaaggg tcgatgcagg cgtctgtggg                    40

<210> SEQ ID NO 18
<211> LENGTH: 41
<212> TYPE: DNA
<213> ORGANISM: Artificial Sequence
<220> FEATURE:
<223> OTHER INFORMATION: randomized sequence

<400> SEQUENCE: 18
acctccatgt caatatcatc agtatcaaaa tgggtgctgg g                  41

<210> SEQ ID NO 19
<211> LENGTH: 40
<212> TYPE: DNA
<213> ORGANISM: Artificial Sequence
<220> FEATURE:
<223> OTHER INFORMATION: randomized sequence

<400> SEQUENCE: 19
aaccaacttt tttcaaacac tcactatctg ggtgtatggg                    40

<210> SEQ ID NO 20
<211> LENGTH: 40
<212> TYPE: DNA
<213> ORGANISM: Artificial Sequence
<220> FEATURE:
<223> OTHER INFORMATION: randomized sequence

<400> SEQUENCE: 20
cactccttcg caacaccact caccttggga ccttgggtgg                    40

<210> SEQ ID NO 21
<211> LENGTH: 40
<212> TYPE: DNA
<213> ORGANISM: Artificial Sequence
<220> FEATURE:
<223> OTHER INFORMATION: randomized sequence

<400> SEQUENCE: 21
gcaggcactc tcactcaagg gtcgatcagg cgtctgtggg                    40

<210> SEQ ID NO 22
<211> LENGTH: 40
<212> TYPE: DNA
<213> ORGANISM: Artificial Sequence
```

```
<220> FEATURE:
<223> OTHER INFORMATION: randomized sequence

<400> SEQUENCE: 22
atgactgact acacatgccc cttagggatg tatcttaggg                           40

<210> SEQ ID NO 23
<211> LENGTH: 40
<212> TYPE: DNA
<213> ORGANISM: Artificial Sequence
<220> FEATURE:
<223> OTHER INFORMATION: randomized sequence

<400> SEQUENCE: 23
aaccaacctc tctcaaaccc tcactatcgg gttgtatggg                           40

<210> SEQ ID NO 24
<211> LENGTH: 40
<212> TYPE: DNA
<213> ORGANISM: Artificial Sequence
<220> FEATURE:
<223> OTHER INFORMATION: randomized sequence

<400> SEQUENCE: 24
accagacgta tccacactca ttgggcttgg tctccgtggg                           40

<210> SEQ ID NO 25
<211> LENGTH: 40
<212> TYPE: DNA
<213> ORGANISM: Artificial Sequence
<220> FEATURE:
<223> OTHER INFORMATION: randomized sequence

<400> SEQUENCE: 25
ctactccctc cctaaccctg ggtccgctat acatggtggg                           40

<210> SEQ ID NO 26
<211> LENGTH: 40
<212> TYPE: DNA
<213> ORGANISM: Artificial Sequence
<220> FEATURE:
<223> OTHER INFORMATION: randomized sequence

<400> SEQUENCE: 26
gccgaattca cacatcgggc ccatcgtcga ggtgcgtggg                           40

<210> SEQ ID NO 27
<211> LENGTH: 40
<212> TYPE: DNA
<213> ORGANISM: Artificial Sequence
<220> FEATURE:
<223> OTHER INFORMATION: randomized sequence

<400> SEQUENCE: 27
acccctctgc ctcactccaa ttcagcgggc ggttcgtggg                           40

<210> SEQ ID NO 28
<211> LENGTH: 40
<212> TYPE: DNA
<213> ORGANISM: Artificial Sequence
<220> FEATURE:
<223> OTHER INFORMATION: randomized sequence

<400> SEQUENCE: 28
ggtcctacgg actttggcac gcaatcacta ggtgtttggg                           40
```

<210> SEQ ID NO 29
<211> LENGTH: 86
<212> TYPE: DNA
<213> ORGANISM: Artificial Sequence
<220> FEATURE:
<221> NAME/KEY: misc_feature
<222> LOCATION: (1)...(86)
<223> OTHER INFORMATION: n = A,T,C or G
<223> OTHER INFORMATION: randomized sequence

<400> SEQUENCE: 29
gccggatccg ggcctcatgt cgaannnnnn nnnnnnnnnn nnnnnnnnnn nnnnnnnnnn     60
nnnnttgacc gtttattctt gtctcc                                         86

<210> SEQ ID NO 30
<211> LENGTH: 48
<212> TYPE: DNA
<213> ORGANISM: Artificial Sequence
<220> FEATURE:
<223> OTHER INFORMATION: randomized sequence

<400> SEQUENCE: 30
ccgaagctta atacgactca ctatagggag acaagaataa acggtcaa                 48

<210> SEQ ID NO 31
<211> LENGTH: 13
<212> TYPE: DNA
<213> ORGANISM: Artificial Sequence
<220> FEATURE:
<223> OTHER INFORMATION: randomized sequence

<400> SEQUENCE: 31
ccctcatgtc gaa                                                       13

<210> SEQ ID NO 32
<211> LENGTH: 25
<212> TYPE: DNA
<213> ORGANISM: Artificial Sequence
<220> FEATURE:
<223> OTHER INFORMATION: randomized sequence

<400> SEQUENCE: 32
ccaagcggcc tctgataacc aagcc                                          25

<210> SEQ ID NO 33
<211> LENGTH: 25
<212> TYPE: DNA
<213> ORGANISM: Artificial Sequence
<220> FEATURE:
<223> OTHER INFORMATION: randomized sequence

<400> SEQUENCE: 33
cagcaccatc ctcctcttcc tctgg                                          25

<210> SEQ ID NO 34
<211> LENGTH: 30
<212> TYPE: DNA
<213> ORGANISM: Artificial Sequence
<220> FEATURE:
<223> OTHER INFORMATION: randomized sequence

<400> SEQUENCE: 34
tgacggggtc acccacactg tgcccatcta                                     30

<210> SEQ ID NO 35

<211> LENGTH: 29
<212> TYPE: DNA
<213> ORGANISM: Artificial Sequence
<220> FEATURE:
<223> OTHER INFORMATION: randomized sequence

<400> SEQUENCE: 35
ctagaagcat tgcggtggca gatggaggg                                29

<210> SEQ ID NO 36
<211> LENGTH: 86
<212> TYPE: DNA
<213> ORGANISM: Artificial Sequence
<220> FEATURE:
<223> OTHER INFORMATION: randomized sequence
<221> NAME/KEY: misc_feature
<222> LOCATION: (1)...(86)
<223> OTHER INFORMATION: n = A,T,C or G

<400> SEQUENCE: 36
gccggatccg ggcctcatgt cgaannnnnn nnnnnnnnnn nnnnnnnnnn          60
nnnnttgacc gtttattctt gtctcc                                   86

<210> SEQ ID NO 37
<211> LENGTH: 48
<212> TYPE: DNA
<213> ORGANISM: Artificial Sequence
<220> FEATURE:
<223> OTHER INFORMATION: randomized sequence

<400> SEQUENCE: 37
ccgaagctta atacgactca ctatagggag acaagaataa acggtcaa            48

<210> SEQ ID NO 38
<211> LENGTH: 13
<212> TYPE: DNA
<213> ORGANISM: Artificial Sequence
<220> FEATURE:
<223> OTHER INFORMATION: randomized sequence

<400> SEQUENCE: 38
ccctcatgtc gaa                                                 13

<210> SEQ ID NO 39
<211> LENGTH: 25
<212> TYPE: DNA
<213> ORGANISM: Artificial Sequence
<220> FEATURE:
<223> OTHER INFORMATION: randomized sequence

<400> SEQUENCE: 39
ccaagcggcc tctgataacc aagcc                                    25

<210> SEQ ID NO 40
<211> LENGTH: 25
<212> TYPE: DNA
<213> ORGANISM: Artificial Sequence
<220> FEATURE:
<223> OTHER INFORMATION: randomized sequence

<400> SEQUENCE: 40
cagcaccatc ctcctcttcc tctgg                                    25

<210> SEQ ID NO 41
<211> LENGTH: 30
<212> TYPE: DNA

```
<213> ORGANISM: Artificial Sequence
<220> FEATURE:
<223> OTHER INFORMATION: randomized sequence

<400> SEQUENCE: 41
tgacggggtc acccacactg tgcccatcta                                    30

<210> SEQ ID NO 42
<211> LENGTH: 69
<212> TYPE: DNA
<213> ORGANISM: Artificial Sequence
<220> FEATURE:
<223> OTHER INFORMATION: randomized sequence

<400> SEQUENCE: 42
ctagaagcat tgcggtggca gatggagggt gtgggtcgtg ttaagcttcg ggcttcgcgc    60
aaatctggg                                                           69

<210> SEQ ID NO 43
<211> LENGTH: 40
<212> TYPE: DNA
<213> ORGANISM: Artificial Sequence
<220> FEATURE:
<223> OTHER INFORMATION: randomized sequence

<400> SEQUENCE: 43
tctgggtcgt attaagcttc gggcttcgcg caaatctggg                         40

<210> SEQ ID NO 44
<211> LENGTH: 39
<212> TYPE: DNA
<213> ORGANISM: Artificial Sequence
<220> FEATURE:
<223> OTHER INFORMATION: randomized sequence

<400> SEQUENCE: 44
cagtaccggc cacattcccc atcatcatac atgggtggg                          39

<210> SEQ ID NO 45
<211> LENGTH: 40
<212> TYPE: DNA
<213> ORGANISM: Artificial Sequence
<220> FEATURE:
<223> OTHER INFORMATION: randomized sequence

<400> SEQUENCE: 45
ctactagcga gcacgcgctc atcgcgccag tgccattggg                         40

<210> SEQ ID NO 46
<211> LENGTH: 41
<212> TYPE: DNA
<213> ORGANISM: Artificial Sequence
<220> FEATURE:
<223> OTHER INFORMATION: randomized sequence

<400> SEQUENCE: 46
cgagactagc gagcacggct catcggtcga gtgccagaag g                       41

<210> SEQ ID NO 47
<211> LENGTH: 38
<212> TYPE: DNA
<213> ORGANISM: Artificial Sequence
<220> FEATURE:
<223> OTHER INFORMATION: randomized sequence

<400> SEQUENCE: 47
```

-continued ggctcattga cacagactca tcgttgggtc ttgggtgg             38

<210> SEQ ID NO 48
<211> LENGTH: 86
<212> TYPE: DNA
<213> ORGANISM: Artificial Sequence
<220> FEATURE:
<223> OTHER INFORMATION: randomized sequence
<221> NAME/KEY: misc_feature
<222> LOCATION: (1)...(86)
<223> OTHER INFORMATION: n = A,T,C or G

<400> SEQUENCE: 48
gccggatccg ggcctcatgt cgaannnnnn nnnnnnnnnn nnnnnnnnnn nnnnnnnnnn    60
nnnnttgacc gtttattctt gtctcc                                         86

<210> SEQ ID NO 49
<211> LENGTH: 48
<212> TYPE: DNA
<213> ORGANISM: Artificial Sequence
<220> FEATURE:
<223> OTHER INFORMATION: randomized sequence

<400> SEQUENCE: 49
ccgaagctta atacgactca ctatagggag acaagaataa acggtcaa                 48

<210> SEQ ID NO 50
<211> LENGTH: 13
<212> TYPE: DNA
<213> ORGANISM: Artificial Sequence
<220> FEATURE:
<223> OTHER INFORMATION: randomized sequence

<400> SEQUENCE: 50
ccctcatgtc gaa                                                       13

<210> SEQ ID NO 51
<211> LENGTH: 30
<212> TYPE: DNA
<213> ORGANISM: Artificial Sequence
<220> FEATURE:
<223> OTHER INFORMATION: randomized sequence

<400> SEQUENCE: 51
tgacggggtc acccacactg tgcccatcta                                     30

<210> SEQ ID NO 52
<211> LENGTH: 29
<212> TYPE: DNA
<213> ORGANISM: Artificial Sequence
<220> FEATURE:
<223> OTHER INFORMATION: randomized sequence

<400> SEQUENCE: 52
ctagaagcat tgcggtggca gatggaggg                                      29